US012727904B1

(12) United States Patent
James et al.

(10) Patent No.: US 12,727,904 B1
(45) Date of Patent: Sep. 8, 2026

(54) METHOD OF MAKING AN ULTRASONIC SURGICAL INSTRUMENT ASSEMBLY

(71) Applicant: Stryker Corporation, Kalamazoo, MI (US)

(72) Inventors: Megan James, Portage, MI (US); Marc Arthur, Rivers Junction, MI (US)

(73) Assignee: Stryker Corporation, Portage, MI (US)

( * ) Notice: Subject to any disclaimer, the term of this patent is extended or adjusted under 35 U.S.C. 154(b) by 279 days.

(21) Appl. No.: 18/236,362

(22) Filed: Aug. 21, 2023

Related U.S. Application Data

(60) Provisional application No. 63/399,243, filed on Aug. 19, 2022.

(51) Int. Cl.
*B29C 45/16* (2006.01)
*A61B 17/32* (2006.01)
*A61B 17/00* (2006.01)

(52) U.S. Cl.
CPC ...... *A61B 17/320068* (2013.01); *B29C 45/16* (2013.01); *A61B 17/00234* (2013.01)

(58) Field of Classification Search
CPC ................................ B29C 45/14; B29C 45/16
See application file for complete search history.

(56) References Cited

U.S. PATENT DOCUMENTS 4,562,838 A * 1/1986 Walker .............. A61B 18/1402 606/49
6,497,715 B2 12/2002 Satou
6,955,680 B2 10/2005 Satou et al.
6,984,220 B2 1/2006 Wuchinich
7,443,296 B2 10/2008 Mezhinsky et al.
7,568,619 B2 8/2009 Todd et al.
7,796,040 B2 9/2010 Mezhinsky et al.
7,887,559 B2 2/2011 Deng et al.
7,934,648 B2 5/2011 Charles et al.
8,035,487 B2 10/2011 Malackowski
8,157,826 B2 4/2012 Deng et al.
8,820,606 B2 9/2014 Hodgkinson
8,882,657 B2 11/2014 Ohline et al.

(Continued)

FOREIGN PATENT DOCUMENTS

CA 2497733 * 2/2011
CN 1247499 * 3/2000
WO WO9401161 * 1/1994

*Primary Examiner* — Edmund H Lee
(74) *Attorney, Agent, or Firm* — Howard & Howard Attorneys PLLC

(57) ABSTRACT

Ultrasonic surgical instrument assemblies and methods of making ultrasonic surgical instrument assemblies. A single piece carrier defining first and second lumens extending between proximal and distal regions of the single piece carrier is provided. The first lumen includes an irrigation conduit and the second lumen is sized to receive a vibratory component of the ultrasonic surgical instrument. An outer surface of the single piece carrier defines a trench and at least one retention member adjacent the trench. A flexible conductor is positioned within the trench and adjacent the at least one retention member such that the at least one retention member retains the flexible conductor in the trench. The single piece carrier is then overmolded to form an overmold assembly including a distal coupling feature for coupling to a tip sleeve portion of the ultrasonic surgical instrument.

12 Claims, 16 Drawing Sheets

(56) References Cited

U.S. PATENT DOCUMENTS 9,010,610 B2 4/2015 Hodgkinson
9,015,919 B2 4/2015 Beardsley
9,033,251 B2 5/2015 Weisshaupt et al.
9,179,912 B2 11/2015 Yates et al.
9,198,660 B2 12/2015 Hodgkinson
9,592,101 B2 3/2017 Bovet et al.
9,717,565 B2 8/2017 Blair
9,770,855 B2 9/2017 Asselin et al.
10,088,083 B2 10/2018 Foster et al.
10,130,382 B2 11/2018 Gladstone
10,143,513 B2 12/2018 Houser et al.
10,350,024 B2 7/2019 Kube et al.
10,456,137 B2 10/2019 Vendely et al.
10,555,750 B2 2/2020 Conlon et al.
10,588,642 B2 3/2020 Gauthier et al.
10,660,726 B2 5/2020 Blair
10,675,123 B2 6/2020 Bauss et al.
10,736,705 B2 8/2020 Scheib et al.
10,849,714 B2 12/2020 Lehtonen
10,864,059 B2 12/2020 Bauss et al.
10,874,480 B2 12/2020 Mangelberger et al.
10,945,778 B2 3/2021 Weisenburgh, II et al.
10,987,121 B2 4/2021 Gladstone
11,051,866 B2 7/2021 Estera et al.
11,071,604 B2 7/2021 Vargas et al.
11,126,907 B2 9/2021 Johnson
11,191,545 B2 12/2021 Vendely et al.
11,191,553 B2 12/2021 Ketelhohn et al.
11,224,497 B2 1/2022 Shelton, IV et al.
11,227,203 B2 1/2022 Pruckner et al.
11,229,437 B2 1/2022 Shelton, IV et al.
11,241,235 B2 2/2022 Shelton, IV et al.
11,246,678 B2 2/2022 Shelton, IV et al.
11,259,803 B2 3/2022 Shelton, IV et al.
11,291,451 B2 4/2022 Shelton, IV
11,298,127 B2 4/2022 Shelton, IV
11,317,869 B2 5/2022 Aeschlimann et al.
11,317,936 B2 * 5/2022 James ............ A61B 17/320068
11,350,929 B2 6/2022 Giordano et al.
11,350,938 B2 6/2022 Shelton, IV et al.
11,361,176 B2 6/2022 Shelton, IV et al.
11,376,098 B2 7/2022 Shelton, IV et al.
11,389,184 B2 7/2022 Schwamb et al.
11,399,837 B2 8/2022 Shelton, IV et al.
11,426,167 B2 8/2022 Shelton, IV et al.
11,432,904 B2 9/2022 Bauss et al.
11,464,601 B2 10/2022 Shelton, IV et al.
11,484,441 B2 11/2022 McCary et al.
11,553,919 B2 1/2023 Shelton, IV et al.
11,553,971 B2 1/2023 Shelton, IV et al.
11,612,395 B2 3/2023 Yates et al.
11,627,981 B2 4/2023 Cowley
11,638,587 B2 5/2023 Shelton, IV et al.
11,660,163 B2 5/2023 Shelton, IV et al.
11,684,369 B2 6/2023 Shelton, IV et al.
11,684,434 B2 6/2023 Shelton, IV
11,690,605 B2 7/2023 Houser et al.
11,744,583 B2 9/2023 Shelton, IV et al.
11,744,593 B2 9/2023 Shelton, IV et al.
11,752,275 B2 9/2023 Bauss et al.
11,839,397 B2 * 12/2023 Drewek ......... A61B 17/320068
12,251,123 B2 * 3/2025 Drewek ......... A61B 17/320068
12,496,086 B2 * 12/2025 James ............ A61B 17/320068
2016/0241961 A1 * 8/2016 Josefsson ............... H03G 5/005
2017/0071621 A1 3/2017 Downey et al.
2017/0354429 A1 * 12/2017 Ketelhohn .............. A61M 1/77
2018/0056328 A1 3/2018 Downey et al.
2019/0159793 A1 5/2019 Cotter et al.
2020/0093507 A1 * 3/2020 James ............ A61B 17/320068
2020/0129267 A1 4/2020 Lento
2020/0155171 A1 5/2020 Gauthier et al.
2020/0308319 A1 10/2020 Schmid et al.
2020/0345388 A1 11/2020 Downey et al.
2021/0065857 A1 3/2021 Newman et al.
2021/0204936 A1 7/2021 Meyer et al.
2021/0346078 A1 11/2021 Estera
2021/0353350 A1 11/2021 Leuck et al.
2021/0358609 A1 11/2021 Begg et al.
2021/0369295 A1 12/2021 Cowley
2022/0087699 A1 3/2022 Ketelhohn et al.
2022/0287798 A1 9/2022 Minutoli
2022/0296337 A1 9/2022 Minutoli
2022/0313383 A1 10/2022 Minutoli
2022/0361979 A1 11/2022 Bauss et al.
2022/0409432 A1 12/2022 Mccary et al.
2023/0181840 A1 6/2023 Rivier et al.
2023/0252257 A1 8/2023 Hoegerle et al.
2023/0270952 A1 8/2023 Bauss et al.

* cited by examiner 16
256
14
254
28
12
10
26

16
18
44
14
10
41
62
28
42
12
40
34
26
32
38
36
30
50
56
68

40
62
42
28
12
34
32
26
36
30
38
52
50
58
56
60
68

12
28
62
40
41
42
120
128B
130
122
128C
126
74
124
128D
252
14
262B
254
256
132
260
262D
272
270
262C
258
268
257
269
266
264
132
262A
54

METHOD OF MAKING AN ULTRASONIC SURGICAL INSTRUMENT ASSEMBLY

RELATED APPLICATIONS

This application claims priority to and all the benefits of U.S. Provisional Patent Application No. 63/399,243, filed Aug. 19, 2022, the entire contents of which are hereby incorporated by reference.

BACKGROUND

As medical professionals strive for reducing the size of incisions and the amount of recovery time required following invasive surgical procedures, the size of surgical instruments used in such procedures have become smaller. Surgical instruments utilized in such procedures often incorporate surgical cutting accessories such as ultrasonic tips, high-speed drills, rotating burs, open-window shavers, and the like. Irrigation and/or aspiration (i.e., suction) is regularly used with surgical cutting accessories to reduce heat and/or remove debris at the surgical site. Irrigation is also frequently utilized to lubricate the cutting accessories.

One example of a surgical instrument that may utilize irrigation and aspiration is an ultrasonic surgical instrument. It is desirable to provide an ultrasonic surgical instrument that is efficient to manufacture, ergonomic, and long-lasting.

SUMMARY

The present disclosure relates generally to an ultrasonic surgical instrument. The ultrasonic surgical instrument may include a handpiece comprising a transducer and a horn, wherein the transducer is configured to manipulate the horn to actuate a cutting tip that is coupled to the horn to cut or remove biological material.

In a first aspect, a method of making an ultrasonic surgical instrument assembly is provided. The method includes providing a single piece carrier defining first and second lumens extending between proximal and distal regions of the single piece carrier, the first lumen including an irrigation conduit and the second lumen sized to receive a vibratory component of the ultrasonic surgical instrument. The outer surface of the single piece carrier defines a trench extending between the proximal and distal regions of the single piece carrier. The outer surface of the single piece carrier also defines at least one retention member adjacent the trench. The method includes positioning a flexible conductor within the trench of the single piece carrier and adjacent the at least one retention member such that the retention member retains the flexible conductor within the trench. The method also includes, after positioning the flexible conductor, overmolding the single piece carrier to form an overmold assembly comprising a distal coupling feature for coupling the overmold assembly to a tip sleeve of the ultrasonic surgical instrument.

In a second aspect, a method of making an ultrasonic surgical instrument assembly is provided. The method includes providing a single piece carrier defining first and second lumens extending between proximal and distal regions of the single piece carrier, the first lumen including an irrigation conduit and the second lumen sized to receive a vibratory component of the ultrasonic surgical instrument. The outer surface of the single piece carrier defines a trench extending between the proximal and distal regions of the single piece carrier. The outer surface further defines at least one post adjacent the trench. The method further includes positioning a flexible conductor within the trench of the single piece carrier and adjacent to the at least one post. The method also includes melting the at least one post to secure the flexible conductor into position within the trench. The method further includes, after melting the at least one post, overmolding the single piece carrier to form an overmold assembly comprising a distal coupling feature for coupling the overmold assembly to a tip sleeve of the ultrasonic surgical instrument.

In a third aspect, a method of making an ultrasonic surgical instrument assembly is provided. The method includes providing a single piece carrier defining first and second lumens extending between proximal and distal regions of the single piece carrier, the first lumen including an irrigation conduit and the second lumen sized to receive a vibratory component of the ultrasonic surgical instrument. The outer surface of the single piece carrier defines a trench extending between the proximal and distal regions of the single piece carrier. The outer surface of the single piece carrier also defines at least one tab extending transversely over the trench. The method also includes positioning a flexible conductor within the trench of the single piece carrier such that the flexible conductor runs under the at least one tab. The method also includes, after positioning the flexible conductor, overmolding the single piece carrier to form an overmold assembly comprising a distal coupling feature for coupling the overmold assembly to a tip sleeve of the ultrasonic surgical instrument.

In a fourth aspect, a method of making an ultrasonic surgical instrument assembly is provided. The method includes providing a carrier including a single piece carrier body defining first and second lumens. The first lumen extends between proximal and distal regions of the single piece carrier body and is sized to receive a vibratory component of the ultrasonic surgical instrument. The second lumen is sized to receive a portion of an irrigation conduit for the ultrasonic instrument and extends between the distal region of the of the single piece carrier body and a trench defined by an outer surface of the single piece carrier body and extending between the proximal and distal regions of the single piece carrier body. The method further includes providing a conductor housing assembly configured to be received in the trench of the single piece carrier body, the conductor housing assembly defining a trench extending between proximal and distal regions of the conductor housing assembly for receiving a flexible conductor. The method also includes inserting the flexible conductor into the trench of the conductor housing assembly, inserting the irrigation conduit into the trench of the single piece carrier body and through the second lumen, and fitting the conductor housing assembly including the flexible conductor into the trench of the single piece carrier body including the irrigation conduit.

Any of the above aspects can be combined in part or in whole.

For any of the above aspects, any one or more of the following implementations are contemplated, individually or in combination:

In one implementation, the method of making an ultrasonic surgical instrument assembly comprises injection molding the single piece carrier defining the first and second lumens, the trench, and the at least one post or tab. In one implementation, the method of making an ultrasonic surgical instrument assembly comprises injection molding the single piece carrier around the irrigation conduit to form the first lumen.

In one implementation, the method of making an ultrasonic surgical instrument assembly comprises inserting the flexible conductor into a proximal slot defined by the single piece carrier at the proximal region of the single piece carrier, the proximal slot being in communication with the trench. In one implementation, the method of making an ultrasonic surgical instrument assembly comprises inserting the flexible conductor into a distal slot defined by the single piece carrier at the distal region of the single piece carrier, the distal slot being in communication with the trench.

In one implementation, the single piece carrier comprises an inner surface defining the second lumen, the inner surface being continuous between the proximal and distal regions of the single piece carrier.

In one implementation, the single piece carrier includes a proximal coupling feature for coupling the single piece carrier to a proximal assembly of the ultrasonic surgical instrument.

These and other configurations, features, and advantages of the present disclosure will be apparent to those skilled in the art. The present disclosure is not intended to be limited to or by these configurations, embodiments, features, and/or advantages.

BRIEF DESCRIPTION OF THE DRAWINGS

Referring now to the drawings, certain examples are shown in detail. Although the drawings represent certain examples, the drawings are not necessarily to scale and certain features may be exaggerated to better illustrate and explain an aspect of an illustrative example. Further, the exemplary illustrations described herein are not intended to be exhaustive or otherwise limiting or restricting to the precise form and configuration shown in the drawings and disclosed in the following detailed description.

DETAILED DESCRIPTION

Figure 1:
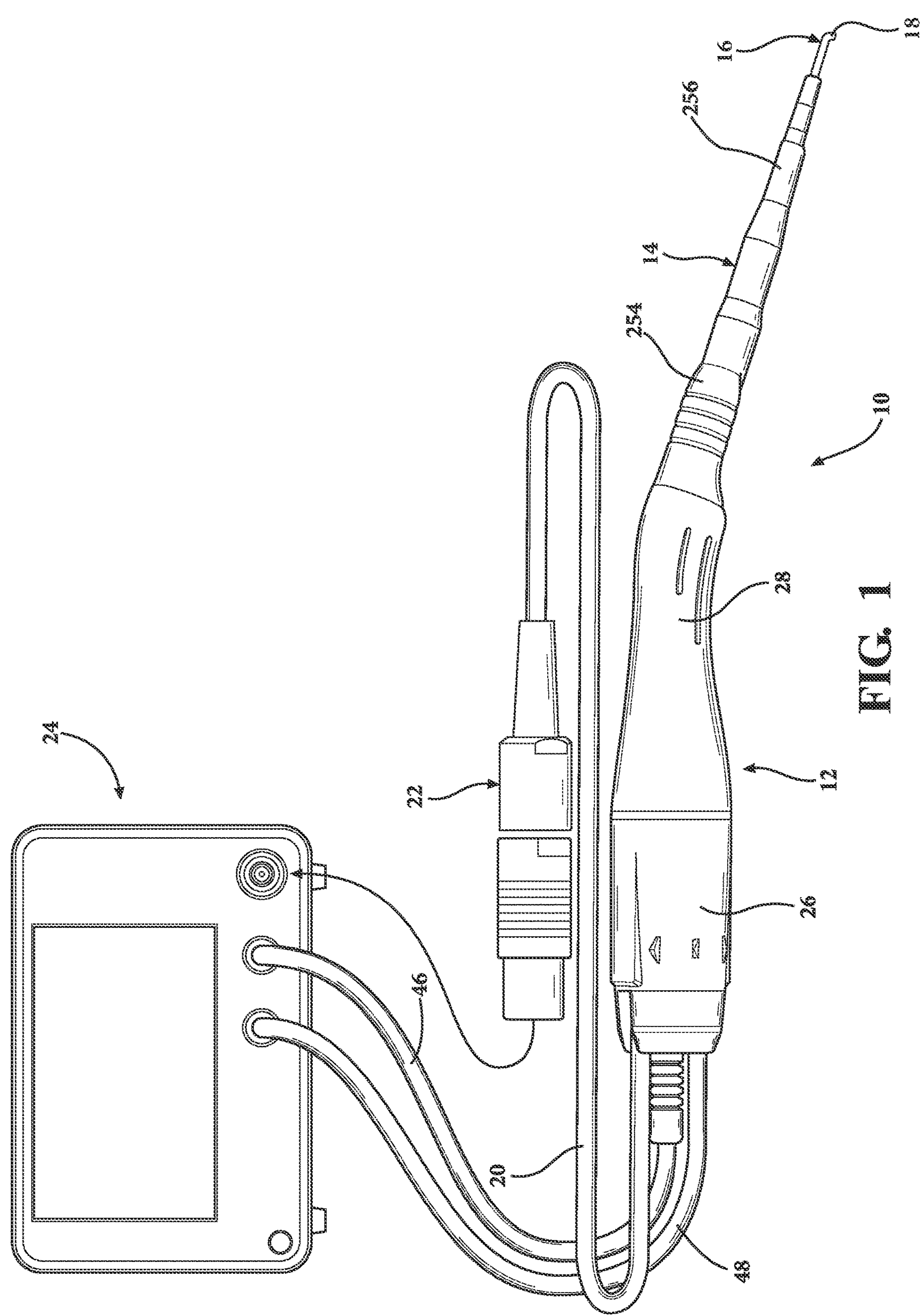
FIG. 1 illustrates an ultrasonic surgical system including an ultrasonic surgical instrument and a control console for driving the ultrasonic surgical instrument.
Figures 2, 3:
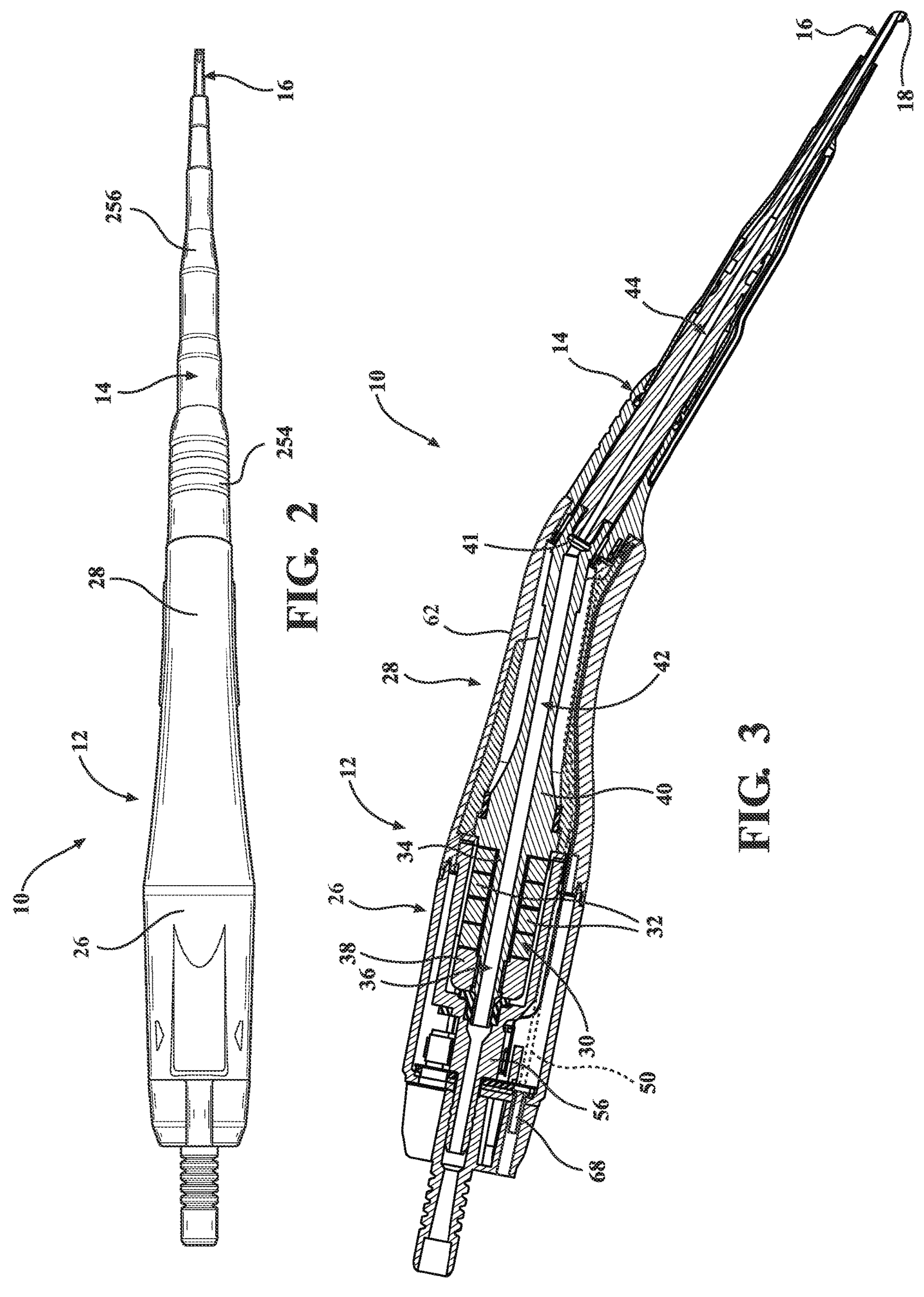
FIG. 2 illustrates a top view of the ultrasonic surgical instrument of FIG. 1.
FIG. 3 illustrates a cross section taken along a longitudinal length of the ultrasonic surgical instrument of FIG. 1.

Referring to FIGS. 1 and 2, an example configuration of an ultrasonic surgical instrument 10 is illustrated. The ultrasonic surgical instrument 10 may comprise an ultrasonic handpiece 12, a sleeve 14 and an ultrasonic tip 16 that may be removably coupled to a distal region of the ultrasonic handpiece 12. The sleeve 14 may be configured to provide irrigation and/or aspiration to the ultrasonic tip 16 and/or the surgical site. The ultrasonic tip 16 may comprise a cutting feature 18 that is configured to cut, shape, and/or remove biological tissue.

The ultrasonic surgical instrument 10 may have various features, such as one or more of those described in U.S. Pat. No. 11,317,936, the disclosure of which is hereby incorporated herein by reference in its entirety. The ultrasonic tip 16 may have various features, such as one or more of those described in U.S. Pat. Nos. 6,497,715; 6,955,680; 6,984,220, the disclosures of which are hereby incorporated herein by reference in their entirety.

The ultrasonic surgical instrument 10 may also comprise a cable 20 or other power cord comprising a power connector 22 or adapter configured to couple the ultrasonic surgical instrument 10 to a power supply, such as a control console 24 configured to regulate the various aspects of the ultrasonic surgical instrument 10. For example, the control console 24 may be configured to regulate the power supplied to the ultrasonic surgical instrument 10, and in turn regulate the vibrations of the tip 16 to resect patient tissue. The control console 24 may also be configured to regulate the power, irrigation and/or aspiration functions of the ultrasonic surgical instrument 10 to optimize its performance.

Figure 4:
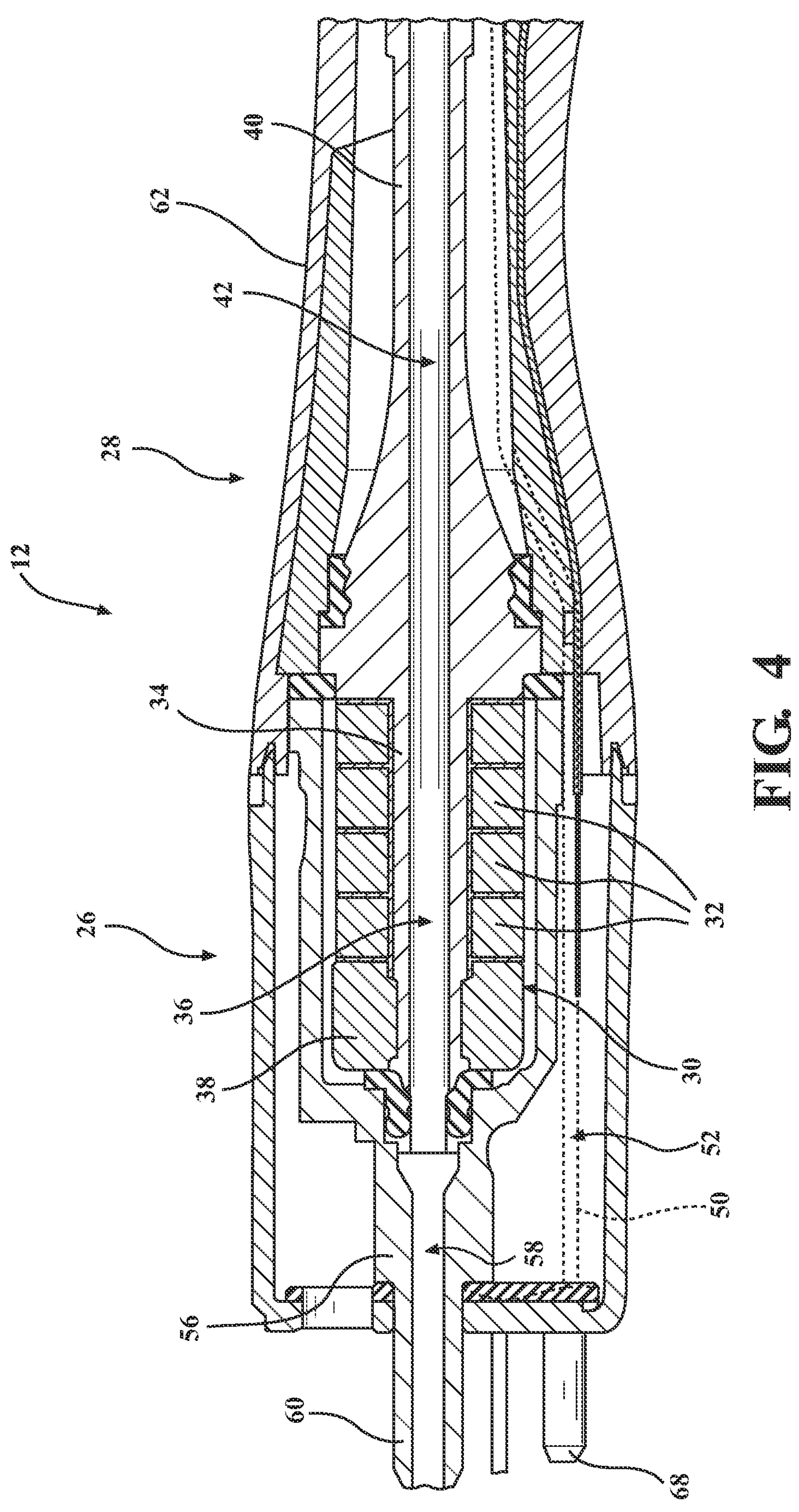
FIG. 4 illustrates a cross section taken along a longitudinal length of a proximal handpiece assembly of the ultrasonic surgical instrument of FIG. 1.

Referring to FIGS. 3 and 4, the ultrasonic handpiece 12 of the ultrasonic surgical instrument 10 may comprise a proximal handpiece assembly 26 and a distal handpiece assembly 28, each of which may define a void that together form a void of the ultrasonic handpiece 12. The proximal handpiece assembly 26 and the distal handpiece assembly 28 may be configured as two separate components, and may be coupled together by a laser weld or similar coupling process. Alternatively, the proximal handpiece assembly 26 and the distal handpiece assembly 28 may include corresponding coupling features configured to couple the proximal handpiece assembly 26 and the distal handpiece assembly 28 together.

A transducer 30 may be disposed in the void defined by the ultrasonic handpiece 12, or more particularly may be at least partially disposed in the void defined by the proximal handpiece assembly 26, which may also be referred to as a transducer handpiece portion of the ultrasonic handpiece 12. The transducer 30 may comprise a plurality of driver elements 32, such as piezoelectric crystals arranged in a stacked configuration. The driver elements 32 may expand and contract based on the application of a varied electrical drive signal from the control console 24. It is further contemplated that the driver elements 32 may be realized as one or more of magnetostrictive elements.

The transducer 30 may also comprise a tube 34 that defines a lumen 36 extending from a proximal end to a distal end of the transducer 30 to create a fluid passageway through the transducer 30. The tube 34 may take the form of a post. The tube 34 may extend through the collinear longitudinal axes of the driver elements 32. A proximal end mass 38 may be located adjacent and/or coupled to the proximal face of the most proximally located driver element 32.

A horn 40 may also be at least partially disposed within the void defined by ultrasonic handpiece 12, or more particularly at least partially disposed within the void defined by the distal handpiece assembly 28. The ultrasonic surgical instrument 10 may be constructed so that the driver elements 32 are compressed between the proximal end mass 38 and the horn 40. To this end, the horn 40 may be coupled to the distal end of the transducer 30. The horn 40 may be constructed from a rigid steel alloy, titanium or similar material. In operation, as the transducer 30 expands and contracts, the horn 40 will oscillate. The horn 40 may be removably coupled to the transducer 30. For example, a proximal region of the horn 40 may comprise a threaded male coupler and a distal region of the transducer 30 may comprise a corresponding female threaded coupler. Alternatively, the transducer 30 and the horn 40 may be permanently coupled via a weld, adhesive, or similar bonding process. The horn 40 may be configured to define a lumen 42 that is in fluid communication with the lumen 36 defined by the tube 34 of the transducer 30 when the horn 40 is coupled to the transducer 30. Collectively, the lumen 36 through the transducer 30 and the lumen 42 through the horn 40 may form at least a portion of a continuous fluid passageway that extends from the distal end of the ultrasonic handpiece 12 to the proximal end of the ultrasonic handpiece 12. This fluid passageway may be utilized to provide irrigation fluid and/or a vacuum through the ultrasonic handpiece 12.

The distal region of the horn 40 may comprise a threaded coupler 41 that is configured to removably couple the ultrasonic tip 16 to ultrasonic handpiece 12 via the horn 40. While the threaded coupler 41 on the distal region of the horn 40 may comprise threads configured to engage corresponding threads on the ultrasonic tip 16, it is further contemplated that other coupling methods may be utilized. For example, the distal region of the horn 40 may comprise features that allow snap fit engagement with the ultrasonic tip 16.

The ultrasonic tip 16 may likewise define a lumen 44 that extends between the tip's 16 proximal and distal ends, such that when the ultrasonic tip 16 is coupled to the horn 40, the lumen 36 through the transducer 30, the lumen 42 through the horn 40, and the lumen 44 through the tip 16 form at least a portion of a continuous fluid passageway extending from the proximal end of the ultrasonic handpiece 12 to the distal end of the ultrasonic tip 16 for providing irrigation fluid and/or vacuum at the distal end of the ultrasonic tip 16.

Referring again to FIG. 1, the control console 24 of the ultrasonic surgical instrument 10 may be configured to source drive signals over the cable 20 to which the ultrasonic handpiece 12 is connected. In many but not all versions of ultrasonic surgical instrument 10, the ultrasonic handpiece 12 and cable 20 may be assembled as a single unit. The drive signals may be applied to the driver elements 32. At any given instant, the same drive signal may be applied to each of the driver elements 32.

The application of the drive signals may cause the driver elements 32 to simultaneously and cyclically expand and contract. In some implementations, the driver elements 32 may be between 1 and 5 cm in length, and the distance, or the amplitude, of movement over a single expansion/contraction cycle of the driver elements 32 may be between 1 and 10 microns, or more. The horn 40 may be configured to amplify this movement. Consequently, the distal end of the horn 40 and, by extension, the ultrasonic tip 16, when moving from the fully contracted position to the fully extended position may move a maximum of 1000 microns and more often 500 microns or less. Some ultrasonic tips 16 may be designed so that the longitudinal extension/contraction of the ultrasonic tip 16 induces a torsional movement in the cutting feature 18. When the ultrasonic handpiece 12 is actuated to cause the cyclic movement of the ultrasonic tip 16, the cutting feature 18 is considered to be vibrating.

The control console 24 may also include a vacuum pump, an irrigation pump, and a controller. The vacuum pump may be coupled to the ultrasonic surgical instrument 10 via aspiration line 46. The irrigation pump may be coupled to the ultrasonic surgical instrument 10 via irrigation line 48.

The control console 24 may have any of the features described in U.S. Patent Publication Nos. 2017/0071621 A1 and 2018/0056328 A1, the disclosures of which are hereby incorporated by reference herein in their entirety.

Referring again to FIGS. 3 and 4, the ultrasonic handpiece 12 may also comprise a conduit 50 that is at least partially disposed within the ultrasonic handpiece 12 and configured to define a lumen 52 through the ultrasonic handpiece 12 for irrigation and/or suction. The lumen 52 defined by the conduit 50 may form a passageway within the ultrasonic handpiece 12 that is in addition to the passageway formed by the lumen 36 of the transducer 30 and the lumen 42 of the horn 40. For example, the lumen 52 formed by the conduit 50 may define at least a portion of an irrigation pathway through the ultrasonic handpiece 12, in which case the conduit 50 may be referred to as an irrigation conduit 50, and the lumen 36 through the transducer 30 and the lumen 42 through the horn 40 may define at least a portion of an aspiration pathway through the ultrasonic handpiece 12. Alternatively, the lumen 52 of the conduit 50 may define at least a portion of an aspiration passageway through the ultrasonic handpiece 12, and the lumen 36 through the transducer 30 and the lumen 42 through the horn 40 may define at least a portion of an irrigation passageway through the ultrasonic handpiece 12.

Figure 16:
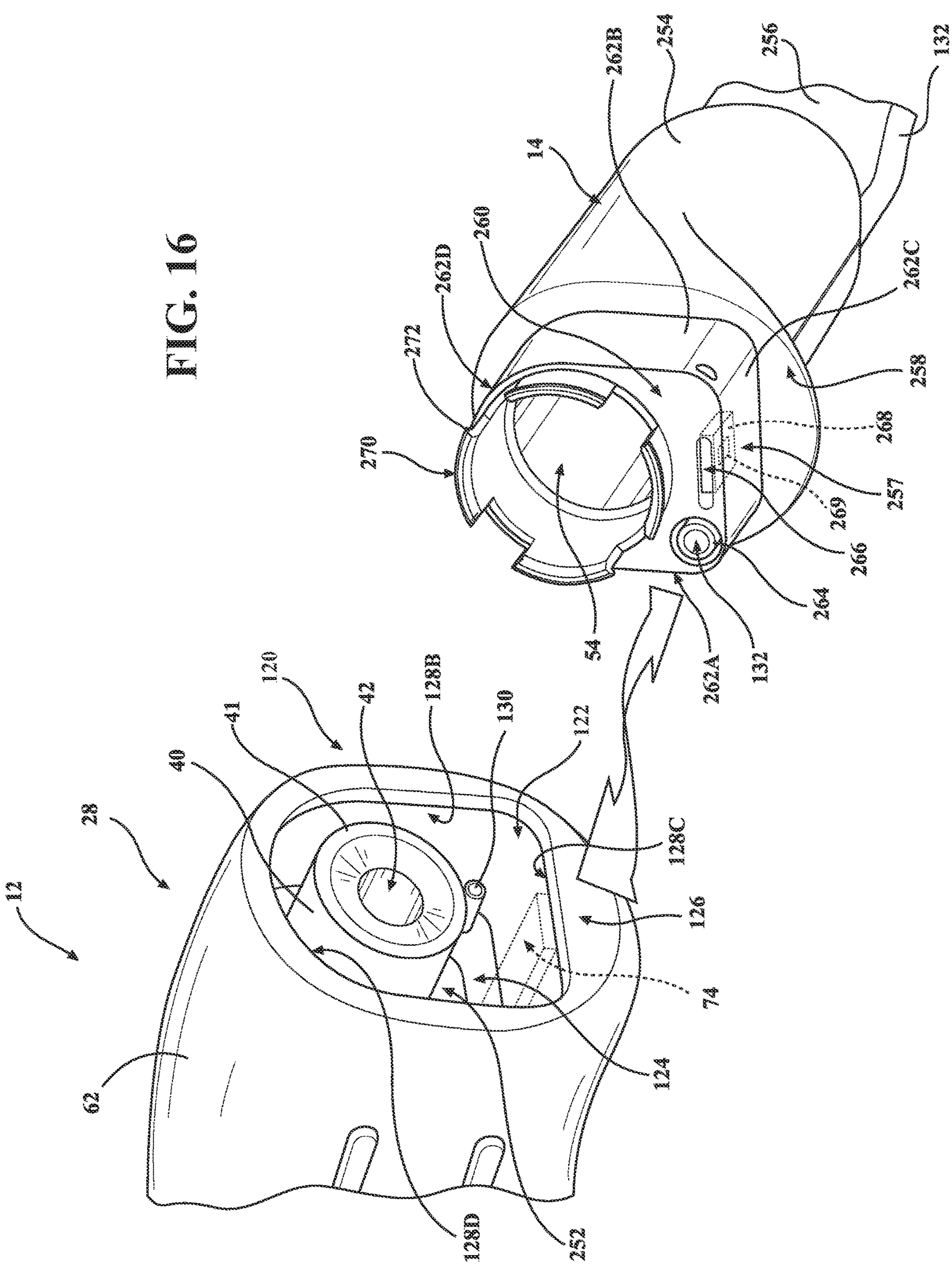
FIG. 16 illustrates an interface for coupling the distal handpiece assembly of FIG. 5 with a tip sleeve that may be incorporated into the ultrasonic surgical instrument of FIG. 1.

As best seen in FIG. 16, the sleeve 14 may define a lumen 54 extending between the proximal and distal ends of the sleeve 14 for receiving the ultrasonic tip 16. More particularly, the sleeve 14 may be configured to be disposed over the ultrasonic tip 16 and coupled to a distal region of the ultrasonic handpiece 12 such that the ultrasonic tip 16 extends through the lumen 54. When coupled to the ultrasonic handpiece 12, the sleeve 14 may be configured so that the sleeve 14 is radially spaced from the ultrasonic tip 16 so as to avoid contact therebetween, and may be configured so that the distal end of the ultrasonic tip 16 extends distally of the distal end of the sleeve 14. Coupling the sleeve 14 to the ultrasonic handpiece 12 may place the lumen 54 defined by the sleeve 14 in fluid communication with the lumen 52 defined by the conduit 50, so as to form a continuous fluid pathway from the proximal end of the ultrasonic handpiece 12 to the distal region of the ultrasonic tip 16.

As shown in the example illustrated in FIG. 4, the ultrasonic handpiece 12, or more particularly the proximal handpiece assembly 26 of the ultrasonic handpiece 12, may include a channel 56 extending in a generally proximal direction from the tube 34. The channel 56 may form a lumen 58 extending through the proximal end of the ultrasonic handpiece 12 and to the tube 34 that defines the lumen 36 through the transducer 30. The channel 56 may further comprise a coupling portion 60, such as a hose barb or similar fitting, that extends proximally from the proximal end of the ultrasonic handpiece 12 and is configured to couple the channel 56 to a line such as the aspiration line 46 from the control console 24. The aspiration line 46 from the control console 24 may thereby apply suction to the distal end of the tip 16 through the fluid pathway defined by the tip 16, horn 40, transducer 30, and channel 56 to remove fluid and/or biological material from the surgical site. Alternatively, in other configurations, the channel 56 may be coupled to the irrigation line 48 via the coupling portion 60, and the irrigation line 48 may be utilized to supply irrigating fluid to the distal end of the tip 16 and the surgical site through the fluid pathway defined by the tip 16, horn 40, transducer 30, and channel 56.

Figure 5:
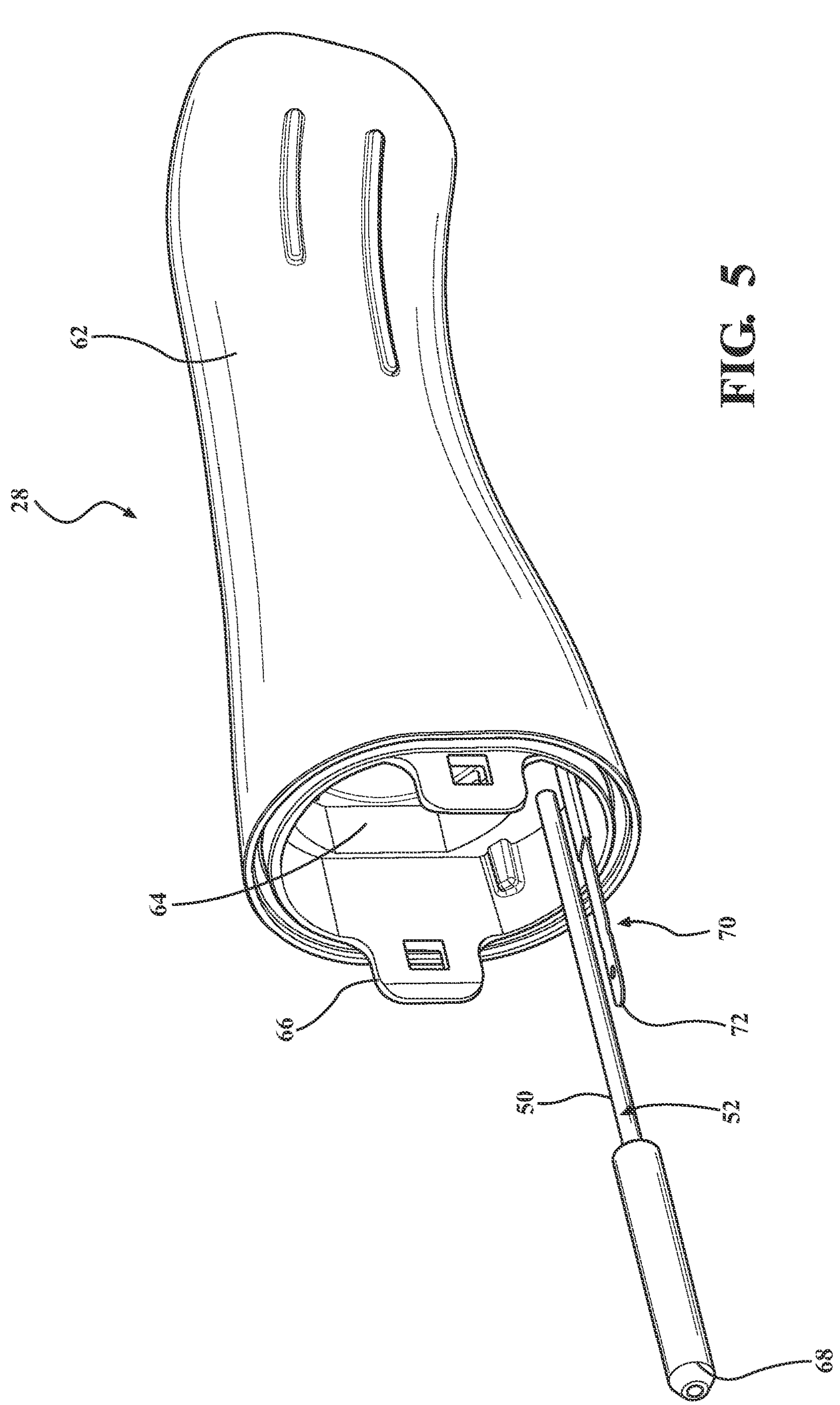
FIG. 5 illustrates distal handpiece assembly that may be incorporated into the ultrasonic surgical instrument of FIG. 1.

FIG. 5 illustrates an exemplary configuration of the distal handpiece assembly 28. The distal handpiece assembly 28 may include an overmold assembly 62 disposed around a single piece carrier 64. The single piece carrier 64 may be defined as a single, monolithic component.

The distal handpiece assembly 28 may comprise a coupling feature 66 configured to removably couple the distal handpiece assembly 28 to a distal end of the proximal handpiece assembly 26 of the ultrasonic handpiece 12. In some instances, the single piece carrier 64 may be integral with or coupled to the coupling feature 66. In other instances, and as shown in the illustrated example, the coupling feature 66 may be integral with or coupled to the overmold assembly 62. In some implementations, the coupling feature 66 may comprise a pair of tabs configured to create a snap and/or friction fit with a corresponding coupling feature of the proximal handpiece assembly 26. Alternative coupling features, such as hooks or protrusions, are also contemplated.

Also illustrated in FIG. 5 is the conduit 50 defining the lumen 52 described above, which may be at least partially disposed within the ultrasonic handpiece 12 so as to maintain the conduit 50 in a specific position and orientation relative to the ultrasonic handpiece 12. More particularly, the conduit 50 may be at least partially disposed within the distal handpiece assembly 28 and the proximal handpiece assembly 26. The conduit 50 may comprise a coupling feature 68, such as a hose barb or similar fitting configured to create a friction fit, positioned at the proximal end of the conduit 50 and extending from the proximal end of the proximal handpiece assembly 26. The coupling feature 68 may be configured to couple the conduit 50 to the irrigation line 48 that is routed from the control console 24 to the ultrasonic surgical instrument 10. The irrigation line 48 from the control console 24 may thereby facilitate the flow of irrigation fluid through the conduit 50 and to the sleeve 14 and/or ultrasonic tip 16. Alternatively, in other configurations, the conduit 50 may be coupled to an aspiration line 46 via the coupling feature 68. The aspiration line 46 may then be utilized to apply suction through the conduit 50, which may be in communication with the sleeve 14 and/or the distal region of the ultrasonic tip 16, to remove biological material and/or fluid from the surgical site.

The distal handpiece assembly 28 of the ultrasonic handpiece 12 may further comprise a flexible conductor 70 (e.g. a flex circuit), which may likewise be at least partially disposed into the single piece carrier 64 so as to maintain a specific position of the flexible conductor 70 relative to the ultrasonic handpiece 12. The flexible conductor 70 may be constructed from an electrically conductive material configured to transmit electrical signals between a distal region and proximal region of the flexible conductor 70. The flexible conductor 70 may comprise an attachment portion 72 positioned at the proximal region of the flexible conductor 70 and configured to couple to a control unit (e.g., processor) disposed within the ultrasonic handpiece 12 when the distal handpiece assembly 28 is coupled to the proximal handpiece assembly 26. The processor may then be configured to communicate with the control console 24 when the ultrasonic surgical instrument 10 is coupled thereto. Alternatively, the attachment portion 72 of the flexible conductor 70 may be configured to couple to a wire, cable, or similar conductor that may couple to the control console 24 via the cable 20.

The flexible conductor 70 may also comprise a transceiver 74 (e.g., FIG. 9A) positioned at the distal region of the flexible conductor 70. As will be described below, the position of the transceiver 74 in the ultrasonic handpiece 12 may be tightly controlled in order to enable the control console 24 to receive signals and/or data from a memory device integral with the sleeve 14 via the flexible conductor 70 when the sleeve 14 is coupled to the ultrasonic handpiece 12. More particularly, the processor or conductor coupled to the proximal region of the flexible conductor 70 may be configured to communicate the electrical signals and/or data between the flexible conductor 70 and the control console 24, which may then control the power supply, irrigation, and/or aspiration functions of the ultrasonic surgical instrument 10 based thereon.

Figure 6A:
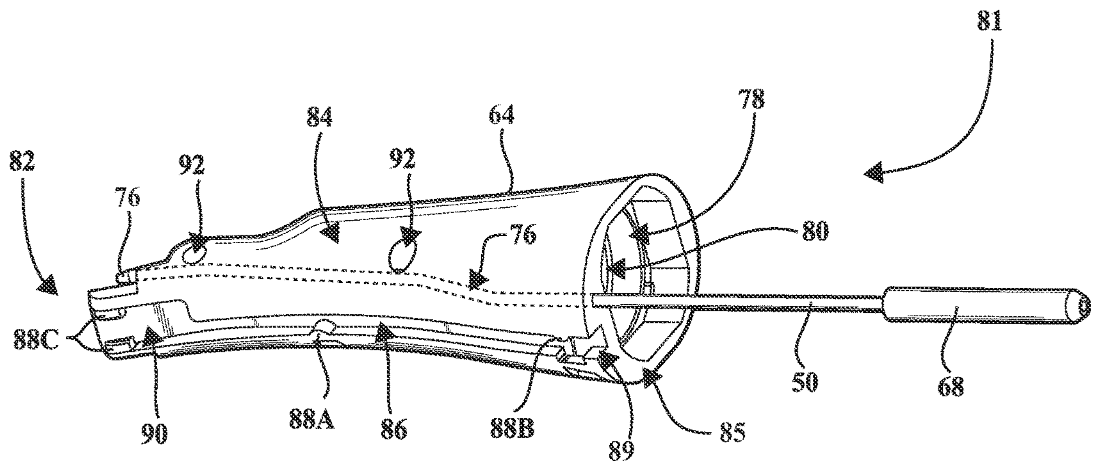
FIGS. 6A and 6B illustrate a single piece carrier that may be incorporated into the distal handpiece assembly of FIG. 5.
Figure 6B:
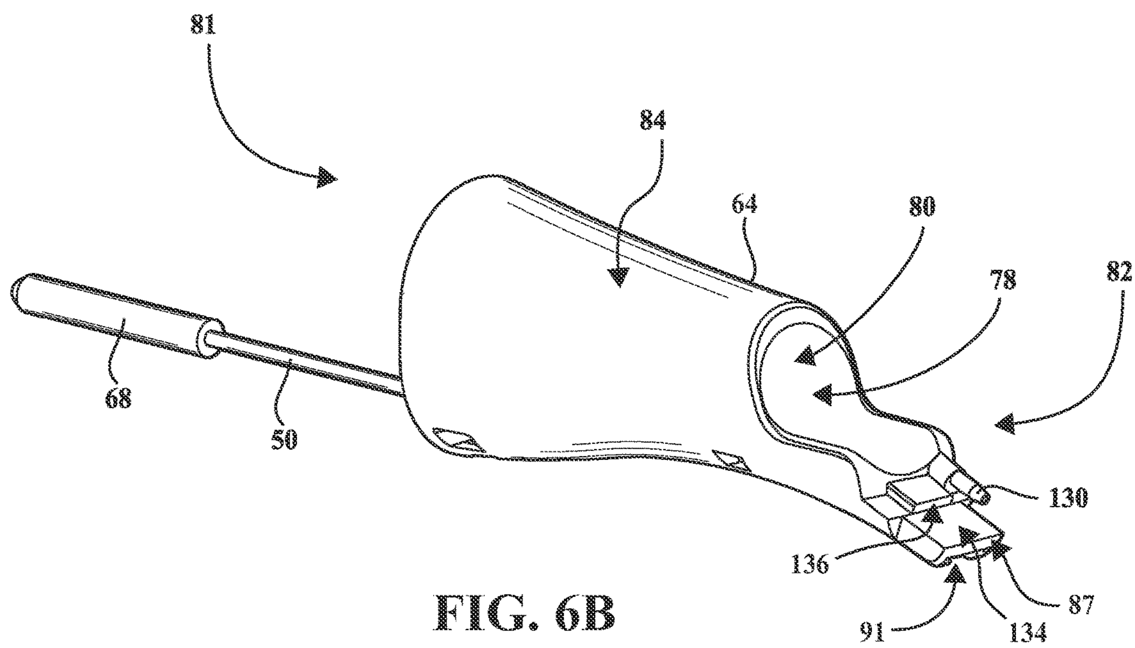

FIGS. 6A and 6B illustrate the single piece carrier 64 that may be incorporated into the distal handpiece assembly 28. The single piece carrier 64 may define a lumen 76 and a lumen 78 each extending between a proximal region 81 and a distal region 82 of the single piece carrier 64. The lumen 76 may be formed to the conduit 50 such as by injection molding, or may be sized to receive the conduit 50, and the lumen 78 may be defined to receive a vibratory component of the ultrasonic surgical instrument 10, such as at least a portion of the transducer 30 and/or at least portion of the horn 40, as shown in FIGS. 3 and 4. The single piece carrier 64 may include an inner surface 80 defining the lumen 78, which may be continuous between the proximal region 81 and distal region 82 of the single piece carrier 64. The single piece carrier 64 may realize increased strength and rigidity relative to a carrier defining a lumen for a vibratory component of an ultrasonic surgical instrument that is formed from a non-continuous surface and/or from multiple components coupled together.

The outer surface 84 of the single piece carrier 64 may define a trench 86 for receiving the flexible conductor 70, and may define at least one tab 88 adjacent the trench 86 for retaining the flexible conductor 70 within the trench 86. In the instance shown in FIGS. 6A and 6B, the single piece carrier 64 includes one tab 88A located approximately halfway between the proximal region 81 and the distal region 82 of the single piece carrier 64, includes a tab 88B at the proximal region 81, and includes a pair of tabs 88C at the distal region 82. It is contemplated that, in other instances, the single piece carrier 64 may include a greater number of tabs 88, which may be equally distributed between the proximal region 81 and the distal region 82 of the single piece carrier 64. Each tab 88 may at least partially extend transversely over the trench 86, and may be configured to retain the flexible conductor 70 in the trench 86 after the trench 86 receives the flexible conductor 70.

The portion of the trench 86 adjacent the distal region 82 of the single piece carrier 64 may include an enlarged section 90 for receiving the transceiver 74 of the flexible conductor 70. Thus, when disposing the flexible conductor 70 in the trench 86 of the single piece carrier 64, the single piece carrier 64 may be configured such that the attachment portion 72 of the flexible conductor 70 is inserted through the trench 86 from the distal region 82 of the single piece carrier 64 under the at least one tab 88 and then out the portion of the trench 86 adjacent the proximal region 81 of the single piece carrier 64, such that the attachment portion 72 extends proximally the proximal region 81 of the single piece carrier 64, and such that the transceiver 74 of the flexible conductor 70 is seated in the enlarged section 90 of the trench 86.

The single piece carrier 64 may include a proximal end face 85 and a distal end face 87, at least one of which may define an access point 89, 91 to an end region of the trench 86 for inserting the flexible conductor 70 into the trench 86. As shown in the illustrated example, such access point 89, 91 may be defined by the trench 86 generally continuing through a periphery of the proximal or distal end face 85, 87, in which case the access point 89, 91 may have a cross-section similar to that of the trench 86 at the access point 89, 91. Alternatively, as described in more detail below, one or both of the proximal and distal end faces 85, 87 may define an access point 89, 91 in the form of a slot with a cross section corresponding to the flexible conductor 70 and in communication with the trench 86 for inserting the flexible conductor 70 into the trench 86.

The single piece carrier 64 may also include one or more minimal through passages 92 extending between the lumen 76 and the outer surface 84 for supporting the irrigation conduit 50 during forming of the single piece carrier 64, as described in more detail below.

Figure 7:
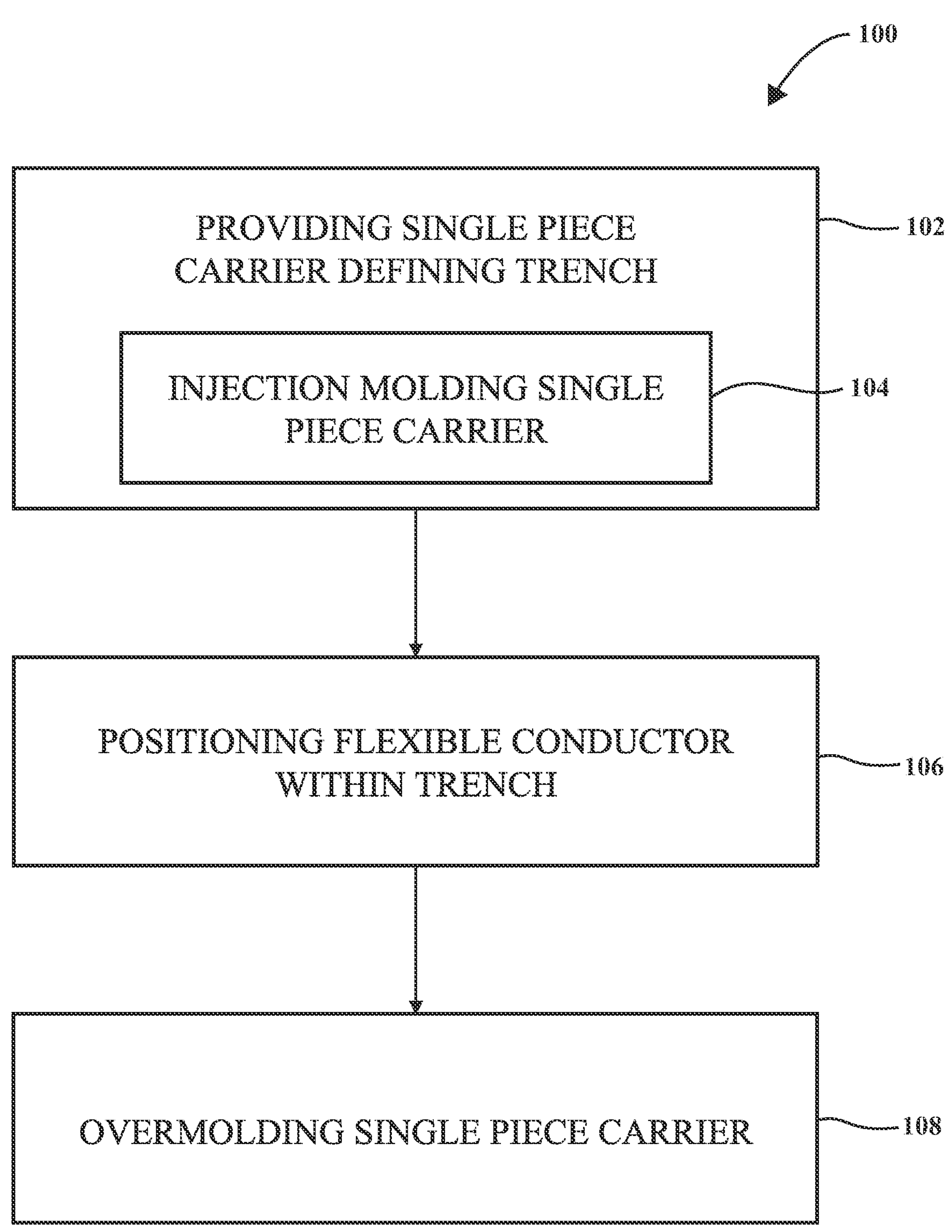
FIG. 7 illustrates a method of making the distal handpiece assembly of FIG. 5.

FIG. 7 illustrates a method 100 of making the distal handpiece assembly 28 including the single piece carrier 64. The method 100 may include a step 102 of providing the single piece carrier 64. The step 102 of providing the single piece carrier 64 may include a step 104 of injection molding the single piece carrier 64. The single piece carrier 64 may be injection-molded from a thermoplastic or similar lightweight and durable material. Step 104 may also include injection molding the single piece carrier 64 with single piece carrier 64 defining the lumens 76, 78, the trench 86, and the at least one tab 88.

In some instances, the single piece carrier 64 may be injected molded around the conduit 50, which may in turn form the lumen 76. To this end, the conduit 50 may be shaped to correspond to the planned shape of the lumen 76, and suspended horizontally or vertically at a planned position within a carrier injection mold tool corresponding to the single piece carrier 64 so as to allow the injected molded material to flow around the conduit 50. To this end, the conduit 50 may be supported at each end region and/or may be supported at one or more intermediate positions corresponding to the through passages 92 extending between the outer surface 84 and the lumen 76 formed around the conduit 50, as illustrated in FIG. 6A.

The carrier injection mold tool may include a pin for forming the lumen 78 through the single piece carrier 64. So as to further aid alignment of the conduit 50 during the injection molding process, a fin-shaped feature may extend radially from the pin adjacent the suspended position of the conduit 50, which may function to form an interior trench 94 (FIG. 8) in the inner surface 80 defining the lumen 78 during the injection molding. The fin may limit upward movement of the conduit 50 and thus aid in positioning the conduit 50 in the desired position during the molding process.

Figure 8:
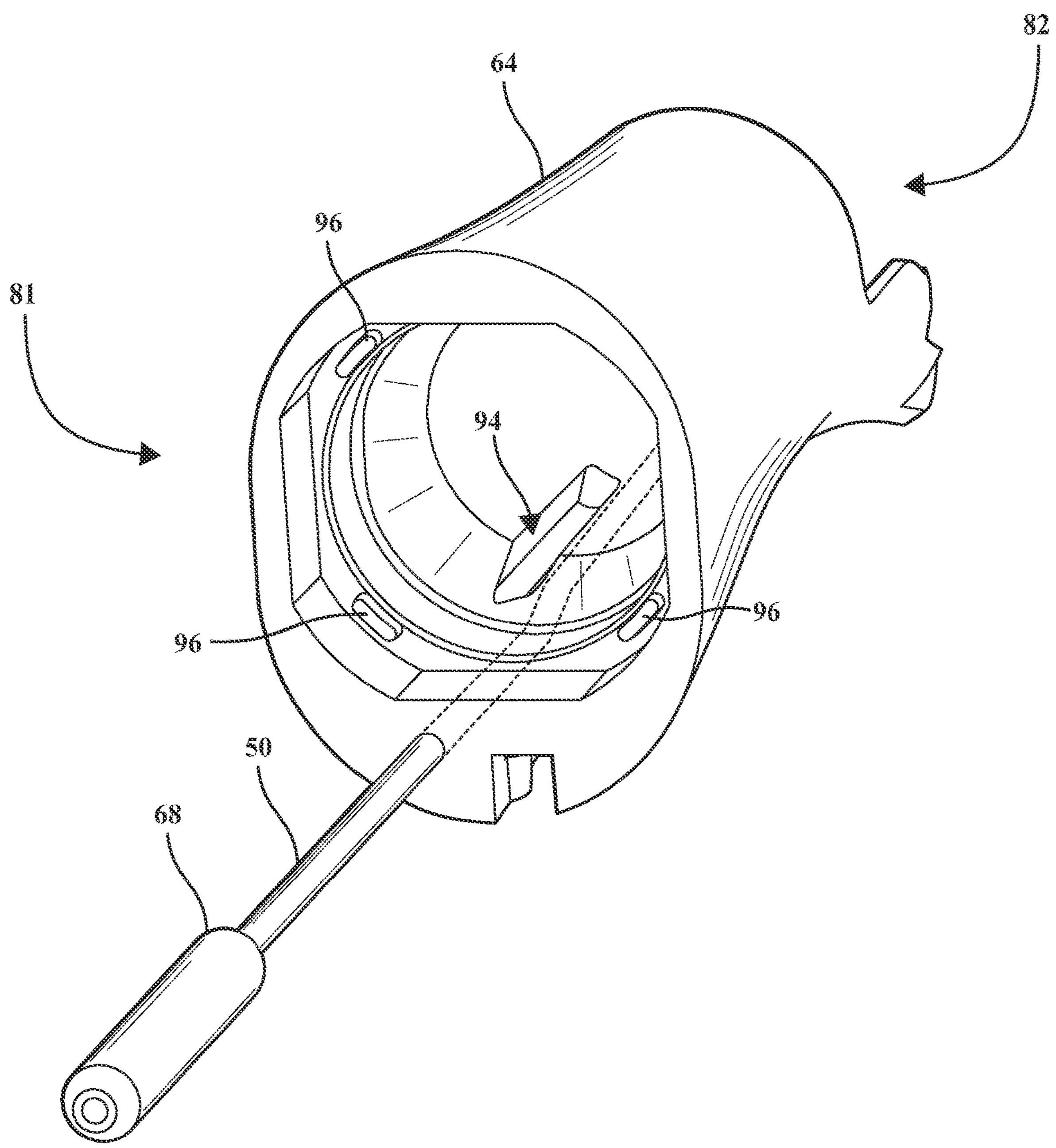
FIG. 8 illustrates a proximal region of the single piece carrier of FIGS. 6A and 6B.

FIG. 8 also illustrates one or more proximally extending protrusions 96 that may be formed integral with the single piece carrier 64. The proximally extending protrusions 96 may be configured to cooperate with corresponding features (e.g., recesses) at the distal end of the transducer 30 to aid in alignment of the transducer 30 during coupling of the distal handpiece assembly 28 to the proximal handpiece assembly 26.

Figures 9A, 9B:
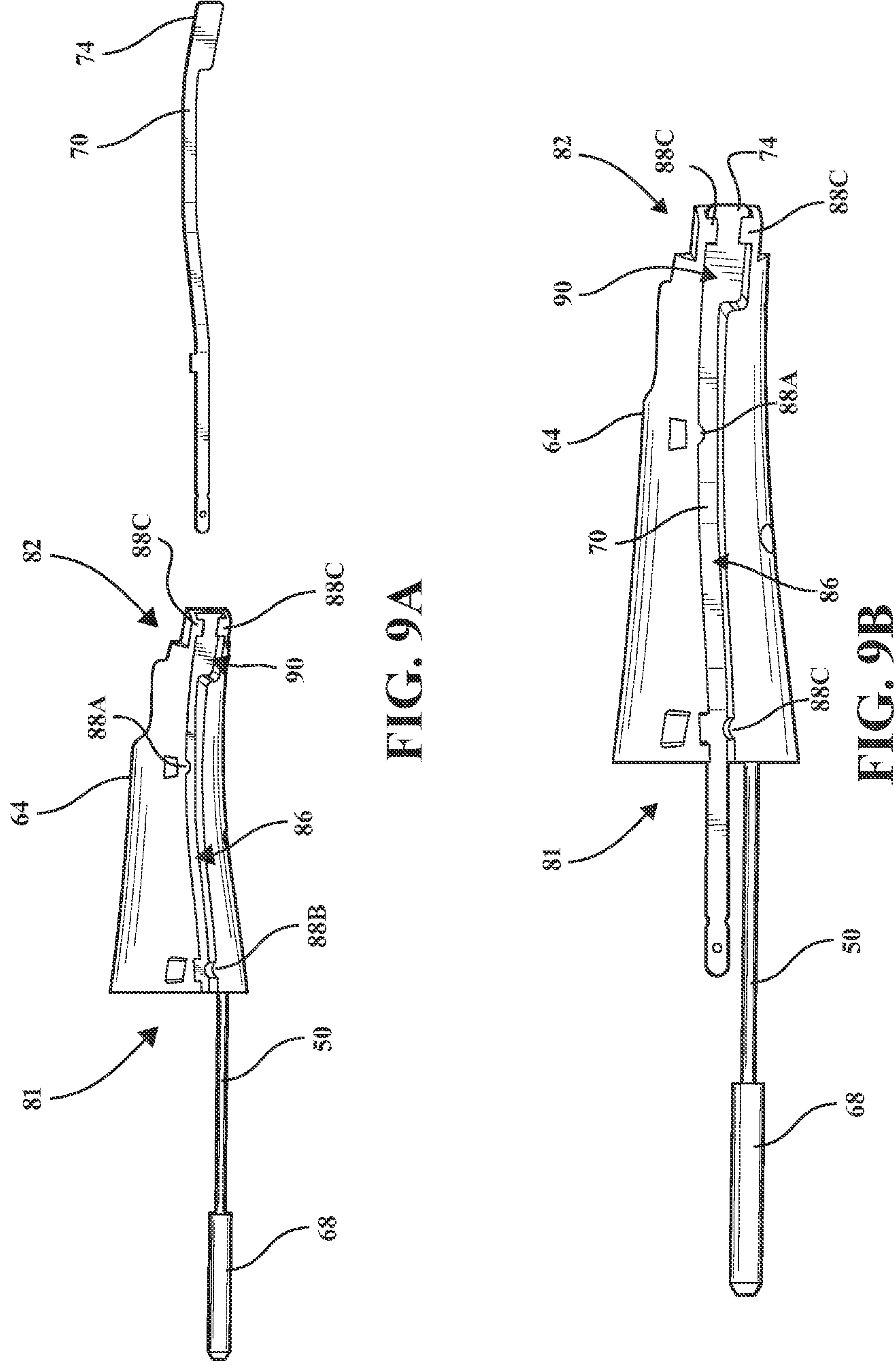
FIG. 9A illustrates the single piece carrier of FIGS. 6A and 6B with a flexible conductor being positioned for insertion into a trench of the single piece carrier.
FIG. 9B illustrates the single piece carrier of FIGS. 6A and 6B with the flexible conductor being positioned within the trench.

Referring again to FIG. 7, the method 100 of making the distal handpiece assembly 28 may also include a step 106 of positioning the flexible conductor 70 within the trench 86 of the single piece carrier 64. FIGS. 9A and 9B illustrate an example of positioning the flexible conductor 70 within the trench 86. As shown in the illustrated example, the flexible conductor 70 may be positioned within the trench 86 such that the flexible conductor 70 runs under the tab(s) 88. Furthermore, the step of positioning the flexible conductor 70 within the trench 86 of the single piece carrier 64 may include the step of sliding the flexible conductor 70, leading with a proximal portion of the flexible conductor 70, into the trench 86 from the distal region 82 of the single piece carrier 64 (e.g., through the access point 91 illustrated in FIG. 6B) until the transceiver 74 is seated in the enlarged section 90 of the trench 86.

The method 100 of making the distal handpiece assembly 28 may also include a step 108 of overmolding the single piece carrier 64 to form the overmold assembly 62 over the single piece carrier 64. The step of overmolding the single piece carrier 64 may occur after the flexible conductor 70 is positioned within the trench 86, and may thus further aid in the retention of the flexible conductor 70 within the trench 86.

In some implementations, the overmold assembly 62 may be formed over the single piece carrier 64 using injection molding. More specifically, the single piece carrier 64 including the flexible conductor 70 and conduit 50 may be placed in an overmold injection mold tool corresponding to the overmold assembly 62, and overmold material may then be injected into the mold tool to form the overmold assembly 62.

Certain portions of the single piece carrier 64, such as the distal region 82, may be susceptible to movement as result of pressure from the overmold material flowing around and pushing inward on the single piece carrier 64. Movement of the single piece carrier 64 relative to the overmold assembly 62 during the molding process may result in connection issues between the distal handpiece assembly 28 and other components of the ultrasonic surgical instrument 10, such as the proximal handpiece assembly 26 and/or the sleeve 14.

Figure 10:
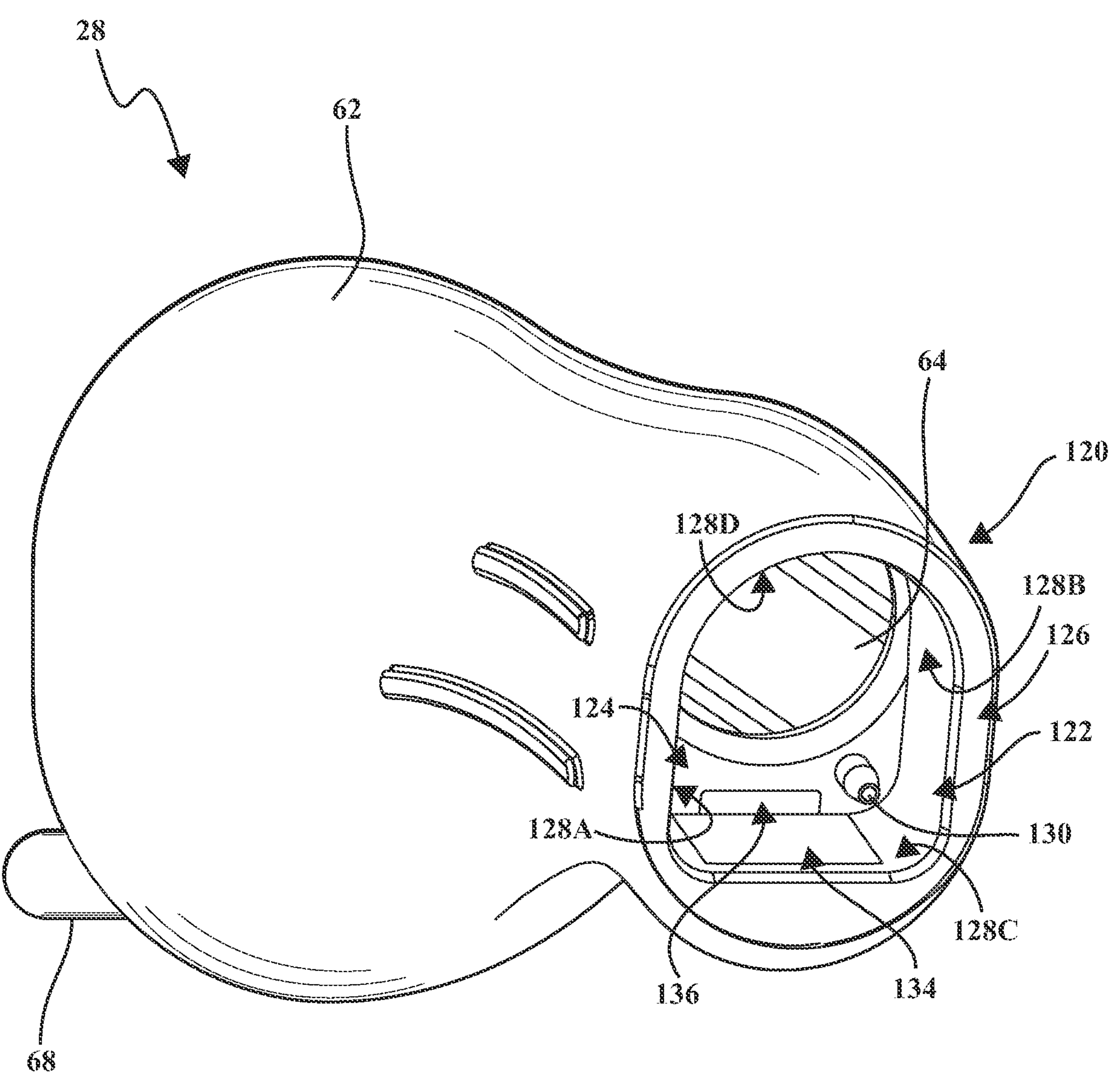
FIG. 10 illustrates a distal region of the distal handpiece assembly of FIG. 5.

For instance, referring FIG. 10, the distal region of the distal handpiece assembly 28 may comprise an attachment region 120, such as formed in the overmold assembly 62, configured to serve as the interface between the ultrasonic handpiece 12 and the sleeve 14 and/or the ultrasonic tip 16. The attachment region 120 may comprise a recess 122 defined by a distally-directed face 124 and a distal surface 126 of the overmold assembly 62 that are connected by a plurality of walls 128 extending perpendicular to the distally-directed face 124 and the distal surface 126.

Extending into the recess 122 from the distally-directed face 124 of the overmold assembly 62 may be a coupler 130 positioned at the distal end of the conduit 50. The coupler 130 may comprise a fitting, hose barb, or similar coupling member for coupling the distal end of the conduit 50 to a corresponding conduit 132 (FIG. 16) of the sleeve 14. The coupler 130 may serve as an inlet or an outlet to transport material and/or fluid between the ultrasonic handpiece 12 and sleeve 14. For instance, the coupler 130 may be configured to be in fluid communication with the lumen 52 disposed within the ultrasonic handpiece 12 to provide irrigation fluid to the sleeve 14. Movement of the distal region 82 of the single piece carrier 64 when forming this portion of the overmold assembly 62 may result in the coupler 130 not aligning with the corresponding conduit 132 of the sleeve 14 upon sleeve 14 being coupled to the distal handpiece assembly 28. Such misalignment may result in in leakage or the components not being able to be securely coupled.

To thus prevent distal movement of the single piece carrier 64 relative to the overmold assembly 62 during the molding process, the single piece carrier 64 may formed to include one or more touch off features (e.g., points, surfaces) configured to contact surfaces of the overmold injection mold tool in different planes so as to prevent portions of the single piece carrier 64 supporting or adjacent the tough off points from moving toward such surfaces and/or planes during the injection molding process, and thus enable overmold material to flow between the overmold injection mold tool surfaces and the portions of the single piece carrier 64 around the touch off features. For instance, still referring to FIG. 10 and also in reference to FIG. 6B, the distal region 82 of the single piece carrier 64 may include a generally parallel touch off surface 134 facing a longitudinal axis of the single piece carrier 64 and configured to touch off a surface of the overmold injection mold tool configured to form one of the walls 128 of the recess 122, which may function to limit movement of the distal region 82 of the single piece carrier 64 into the recess 122 during the injection molding process. Additionally or alternatively, the single piece carrier 64 may include a generally perpendicular touch off surface 136 facing a distal end of the single piece carrier 64 (e.g., the distal end face 87) and configured to touch off a surface of the overmold injection mold tool configured to form the distally-directed face 124 of the recess 122 so as to prevent the single piece carrier from moving distally during the injection molding process.

Figure 11A:
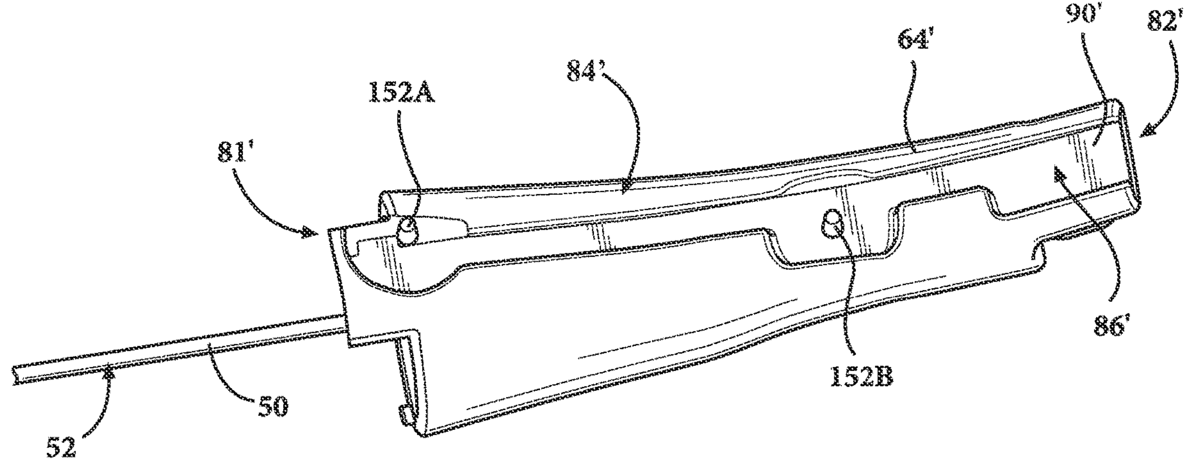
FIG. 11A illustrates an alternative single piece carrier that includes a trench for receiving a flexible conductor and that may be incorporated into the distal handpiece assembly of FIG. 5.
Figure 11B:
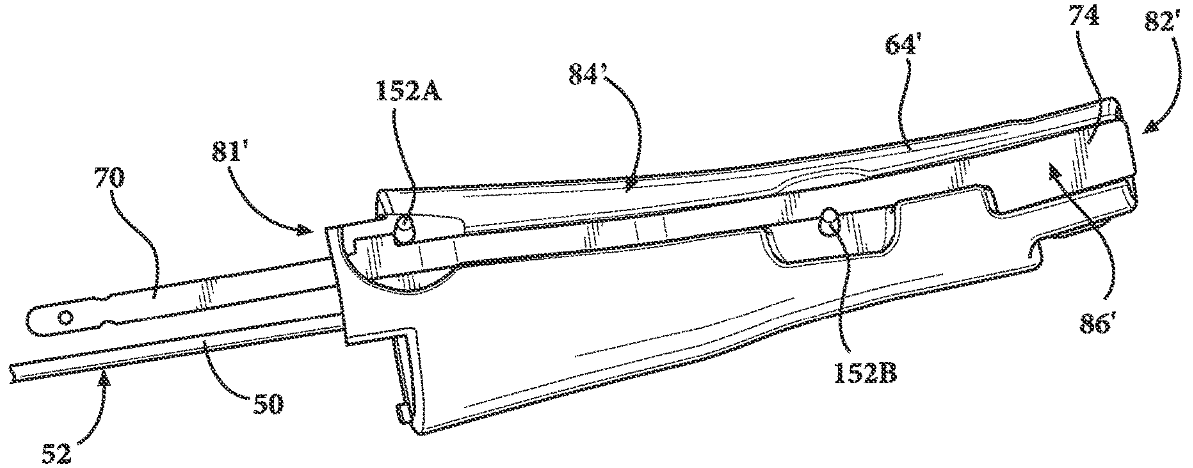
FIG. 11B illustrates the alternative single piece carrier of FIG. 11A with the flexible conductor being positioned within the trench.
Figure 11C:
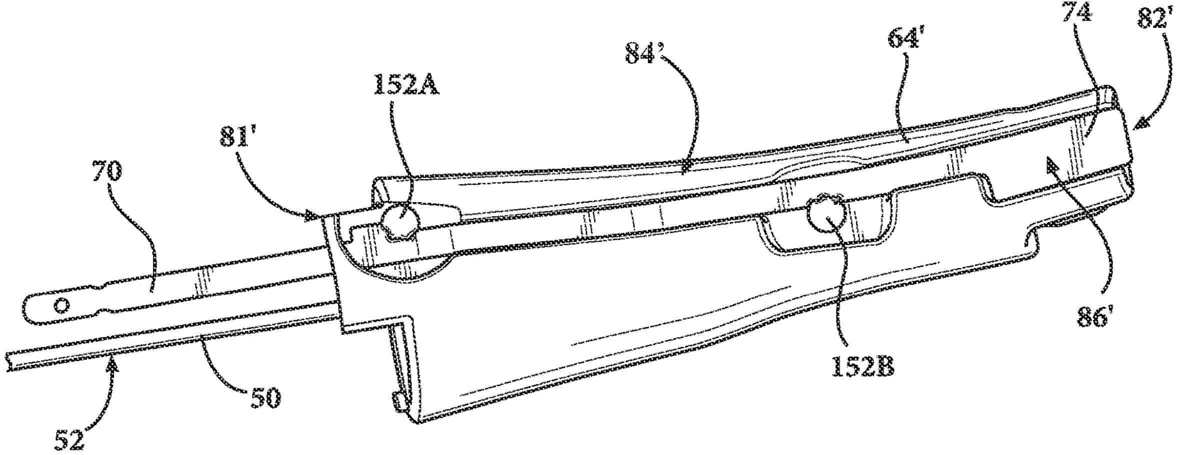
FIG. 11C illustrates the alternative single piece carrier of FIGS. 11A and 11B with at least one post adjacent the trench melted to retain the flexible conductor in the trench.

FIGS. 11A-11C illustrate another exemplary single piece carrier 64' in accordance with the present disclosure. Similar to the single piece carrier 64, the single piece carrier 64' may define a lumen 76' and a lumen 78', each extending between a proximal region 81' and a distal region 82' of the single piece carrier 64'. The lumen 76' may be formed around or sized to receive the conduit 50, and the lumen 78' may be defined to receive a vibratory component of the ultrasonic surgical instrument 10, such as at least a portion of the transducer 30 and/or at least portion of the horn 40, as shown in FIGS. 3 and 4. The single piece carrier 64' may also include an inner surface 80' defining the lumen 78'. Like the inner surface 80 of the single piece carrier 64, the inner surface 80' may be continuous between the proximal and distal regions 81', 82' of the single piece carrier 64', such that single piece carrier 64' does not define an opening or bore extending between an intermediate portion of the lumen 78' and an outer surface 84' of the single piece carrier 64', which provides increased strength and rigidity to the single piece carrier 64'.

The outer surface 84' of the single piece carrier 64' may likewise define a trench 86' for receiving the flexible conductor 70, and may also define at least one post 152 adjacent the trench 86' for retaining the flexible conductor 70 within the trench 86'. In the instance shown in FIGS. 11A-11C, the single piece carrier 64' defines two posts 152, one post 152A being disposed at the proximal region 81' of the single piece carrier 64', and another post 152B at an intermediate portion of the signal piece carrier 64'. It is contemplated that, in other instances, the single piece carrier 64' may define a greater number of posts 152, which may be equally distributed between the proximal region 81' and distal region 82' of the single piece carrier 64', or a single post 152 disposed approximately halfway between the proximal region 81' and the distal region 82'. As shown in FIG. 11C, following placement of the flexible conductor 70 in the trench 86', the post(s) 152 may be melted to secure the flexible conductor 70 into position within the trench 86'.

Figure 12:
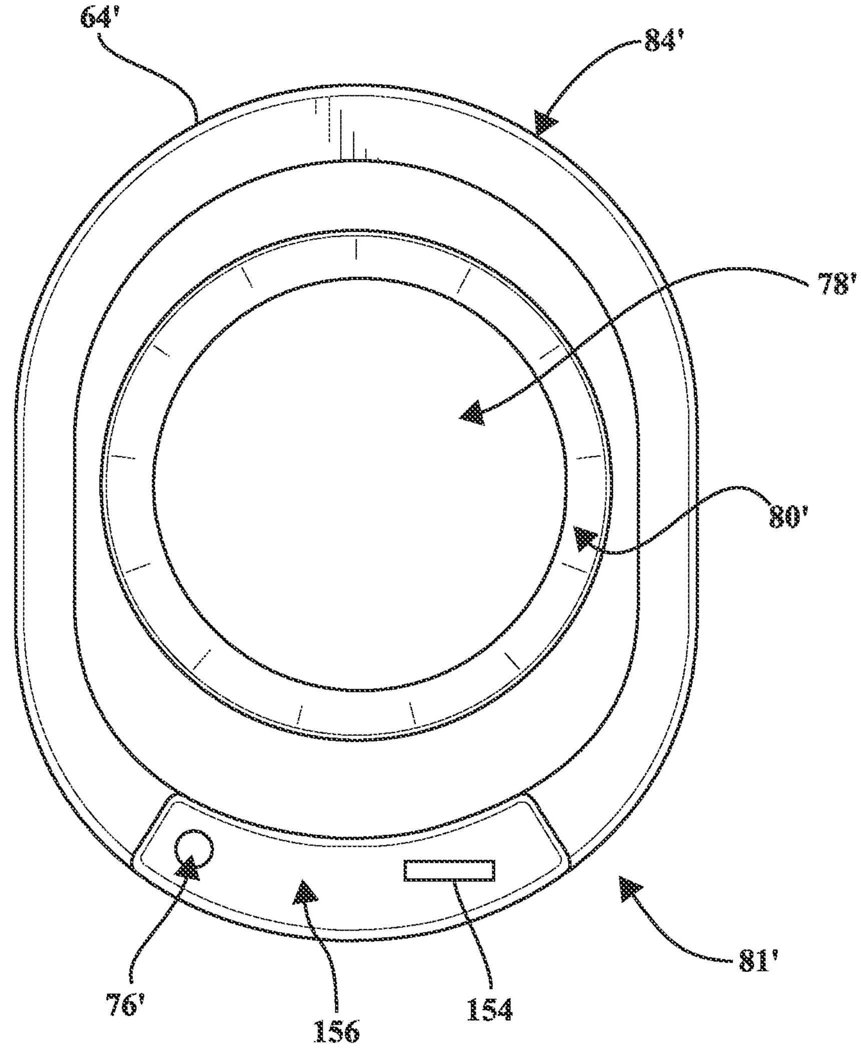
FIG. 12 illustrates a proximal region of the single piece carrier of FIG. 11A.

Referring to FIG. 12, the single piece carrier 64' may define a slot 154 at the proximal region 81' of the single piece carrier 64', or more particularly in a proximal end face 156 of the single piece carrier 64', the proximal slot 154 being in communication with the trench 86'. Additionally or alternatively, the single piece carrier 64' may define a similar slot at the distal region 82' of the single piece carrier 64', or more particularly in a distal end face of the single piece carrier 64', the distal slot being in communication with the trench 86'. The proximal slot 154 and/or the distal slot, along with the trench 86', may be configured to receive the flexible conductor 70. For instance, when disposing the flexible conductor 70 in the trench 86' of the single piece carrier 64', the single piece carrier 64' may be configured such that the attachment portion 72 of the flexible conductor 70 is inserted into the distal slot if present, through the trench 86' adjacent the at least one post 152, and then out the proximal slot 154 if present, such that the attachment portion 72 extends proximally the proximal region 81' of the single piece carrier 64', and/or such that the transceiver 74 of the flexible conductor 70 is positioned within the trench 86' adjacent the distal slot, if present, such as in an enlarged section 90' of the trench 86'. The post(s) 152 may then be melted to secure the flexible conductor 70 into position within the trench 86'.

Figure 13:
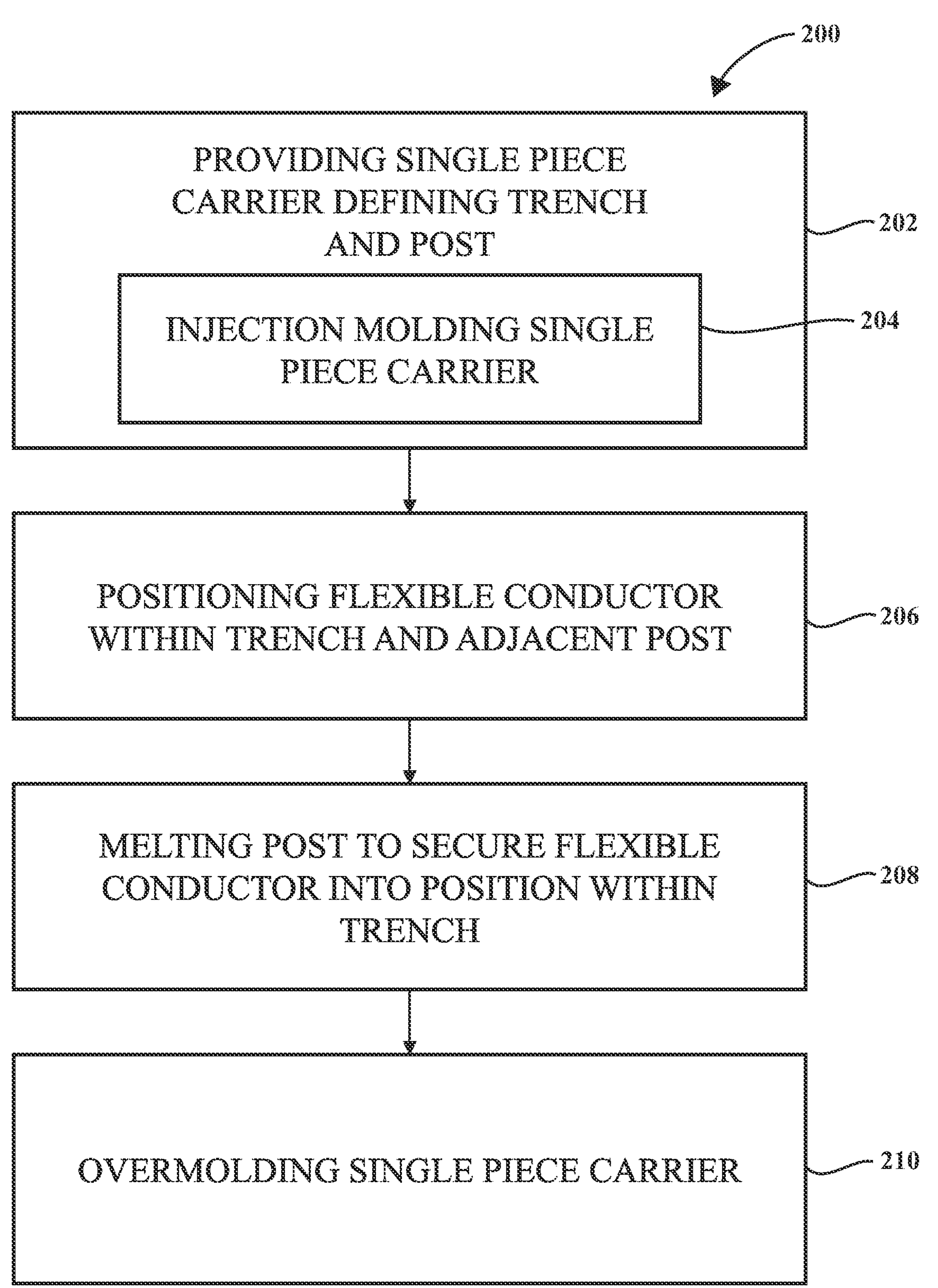
FIG. 13 illustrates a method of making a distal handpiece assembly including the alternative single piece carrier of FIGS. 11A-11C.

FIG. 13 illustrates a method 200 of making the distal handpiece assembly 28 including the single piece carrier 64'. The method 200 may include a step 202 of providing the single piece carrier 64'. The step 202 of providing the single piece carrier 64' may include a step 204 of injection molding the single piece carrier 64'. The single piece carrier 64' may be injection-molded from a thermoplastic or similar lightweight and durable material. Step 204 may include injection molding the single piece carrier 64' with the single piece carrier 64' defining the lumens 76', 78', the trench 86', and the at least one post 152. The single piece carrier 64' may also be injection molded to define the previously described proximal slot 154 and/or distal slot. In some instances, step 204 may also include injection molding the single piece carrier 64' around the conduit 50.

The method 200 of making the distal handpiece assembly 28 may also include a step 206 of positioning the flexible conductor 70 within the trench 86' and adjacent the at least one post 152 of the single piece carrier 64'. FIGS. 11A and 11B illustrate an example of positioning the flexible conductor 70 within the trench 86'. Furthermore, the step 206 of positioning the flexible conductor 70 within the trench 86' may include a step of inserting the flexible conductor 70 into the proximal slot 154 and/or distal slot, as described above.

The method 200 of making the distal handpiece assembly 28 may also include a step 208 of melting the post(s) 152 to secure the flexible conductor 70 into position within the trench 86'. The melted post(s) 152 are shown in FIG. 11C.

The method of making the distal handpiece assembly 28 may also include a step 210 of overmolding the single piece carrier 64' to form the overmold assembly 62 over the single piece carrier 64'. Step 210 of overmolding the single piece carrier 64' may occur after the flexible conductor 70 is positioned within the trench 86' and after the post(s) 152 are melted.

Figure 14:
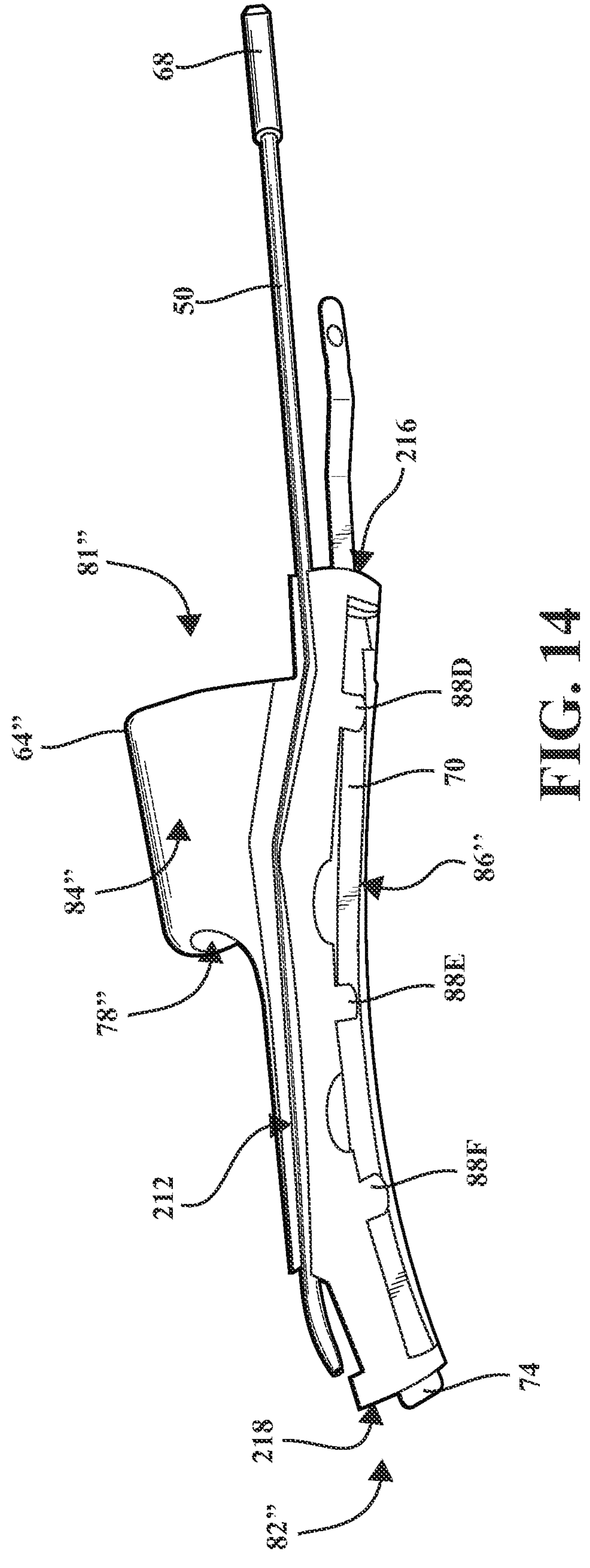
FIG. 14 illustrates another single piece carrier that includes a trench for receiving a flexible conductor that may be incorporated into the distal handpiece assembly of FIG. 5.

FIG. 14 illustrates another single piece carrier 64" in accordance with the present disclosure. Similar to the single piece carrier 64, the single piece carrier 64" may define a lumen a lumen 78" extending between a proximal region 81" and a distal region 82" of the single piece carrier 64". The lumen 78" may be sized to receive a vibratory component of the ultrasonic surgical instrument 10, such as at least a portion of the transducer 30 and/or at least portion of the horn 40, as shown in FIGS. 3 and 4. Like the lumen 78 of the single piece carrier 64, the lumen 78" may be fully defined by the single piece carrier 64", which may increase its strength and rigidity relative to a carrier including such a lumen constructed from multiple components assembled together.

The outer surface 84" of the single piece carrier 64" may define a trench 86" for receiving the flexible conductor 70, and may also define at least one tab 88 adjacent the trench 86" for retaining the flexible conductor 70 within the trench 86" as described above. Similar to the single piece carrier 64 illustrated in FIGS. 11A-11C and FIG. 12, the single piece carrier 64" may also define one or more slots in communication with the trench 86" in a proximal end face 216 and/or distal end face 218 of the single piece carrier 64", respectively, for receiving the flexible conductor 70. In other words, to insert the flexible conductor 70 into the trench 86", the proximal end of the flexible conductor 70 may be inserted into the slot of the distal end face 218, through the trench 86" and under the tab(s) 88, and then to the slot of the proximal end face 216 such that the transceiver 74 is seated in or adjacent the slot of the distal end face 218.

The single piece carrier 64" may also define another trench 212 in its outer surface 84" that is sized and shaped to receive the irrigation conduit 50. Once the irrigation conduit 50 has been received in the trench 212 and the flexible conductor 70 has been received in the trench 86" as described above, the single piece carrier 64" may be overmolded with an overmold assembly 62 as described above to form the distal handpiece assembly 28. In some implementations, an adhesive may be applied to the trench 212 to limit movement of the irrigation conduit 50 during the application of the overmold assembly 62.

As shown in the illustrated examples, the trenches 86, 86', 86" of the single piece carriers 64, 64' may each have a cross-section along its length such that a portion of the perimeter of the cross section that faces the lumen 78, 78', 78" is bounded by the outer surface 84, 84', 84" of the single piece carrier 64, 64', 64" and a portion of the perimeter of the cross section that faces away from the lumen 78, 78', 78" is open. In some examples, the trench 86, 86', 86" may exhibit a rectangular cross-section to match the cross-section shape of the flexible conductor 70, which may also feature a rectangular cross section in the region where the flexible conductor 70 is disposed in the trench 86, 86', 86". However, in other instances, the trench 86, 86', 86" may include a curvilinear shape as defined by the outer surface 84, 84', 84" of the single piece carrier 64, 64', 64". Furthermore, the shape of the trench 86, 86', 86" may be based on a desired shape of the flexible conductor 70.

It should be noted that using one of the single piece carriers 64, 64', 64" to form the distal handpiece assembly 28 in accordance with the present disclosure provides several advantages, such as manufacturing efficiency, improved ergonomics, and increased longevity. For example, because the single piece carriers 64, 64', 64" are single, monolithic components, the single piece carriers 64, 64', 64" may be provided using a single injection mold and thus reduce the assembly or joining of separate sub-components to form the distal handpiece assembly 28, which in turn reduces susceptibility to leakage. Alternatively, the single piece carriers 64, 64', 64" may be produced using additive manufacturing (e.g., 3D printing) or machining techniques to achieve similar effects. The single piece carriers 64, 64', 64" also each includes an increased structural rigidity relative to a multi-component carrier, which is more prone to structural weakness and break down due to deformation, misalignment, and/or variability of individual components during the manufacturing process. The increased uniformity of the single piece carriers 64, 64', 64" relative to a multi-component carrier also enables the provision of distal handpiece assemblies 28 of increased uniformity, including the provision of overmold assemblies 62 with consistent wall thickness along their length.

Figure 15A:
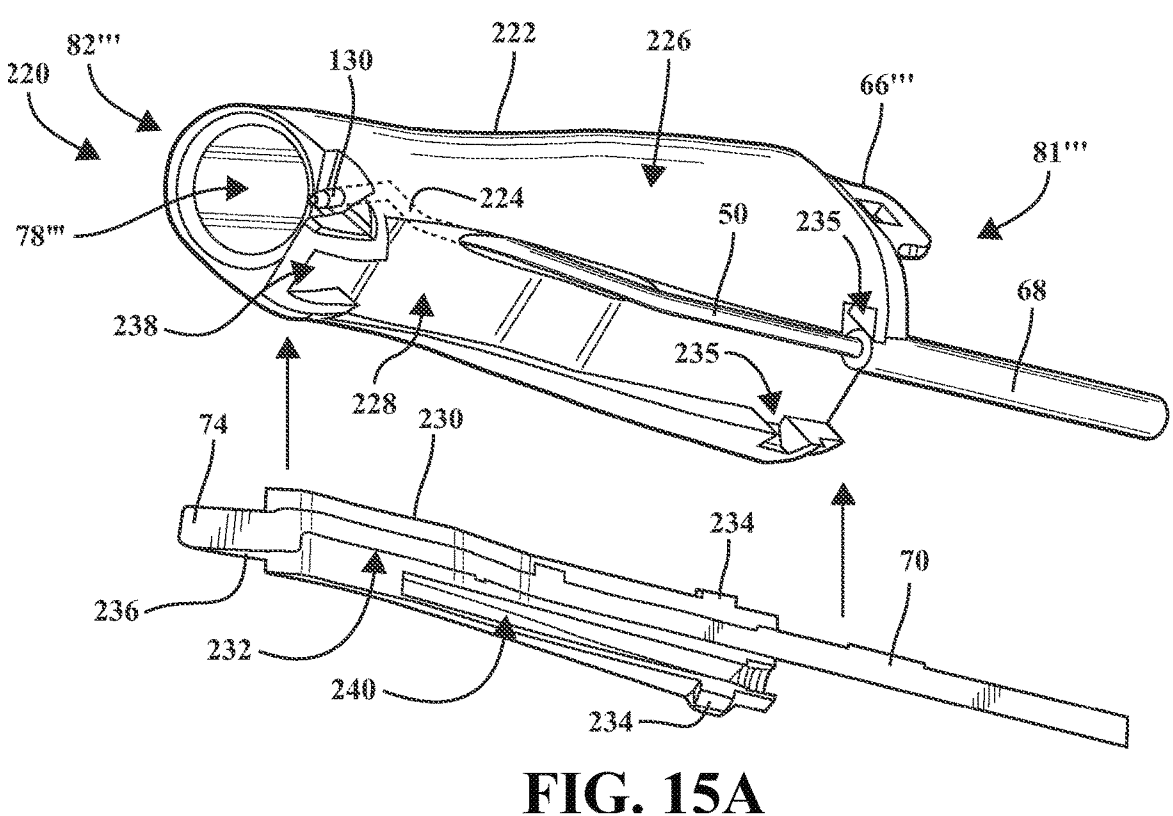
FIGS. 15A and 15B illustrate another carrier that may be incorporated into the distal handpiece assembly of FIG. 5.
Figure 15B:
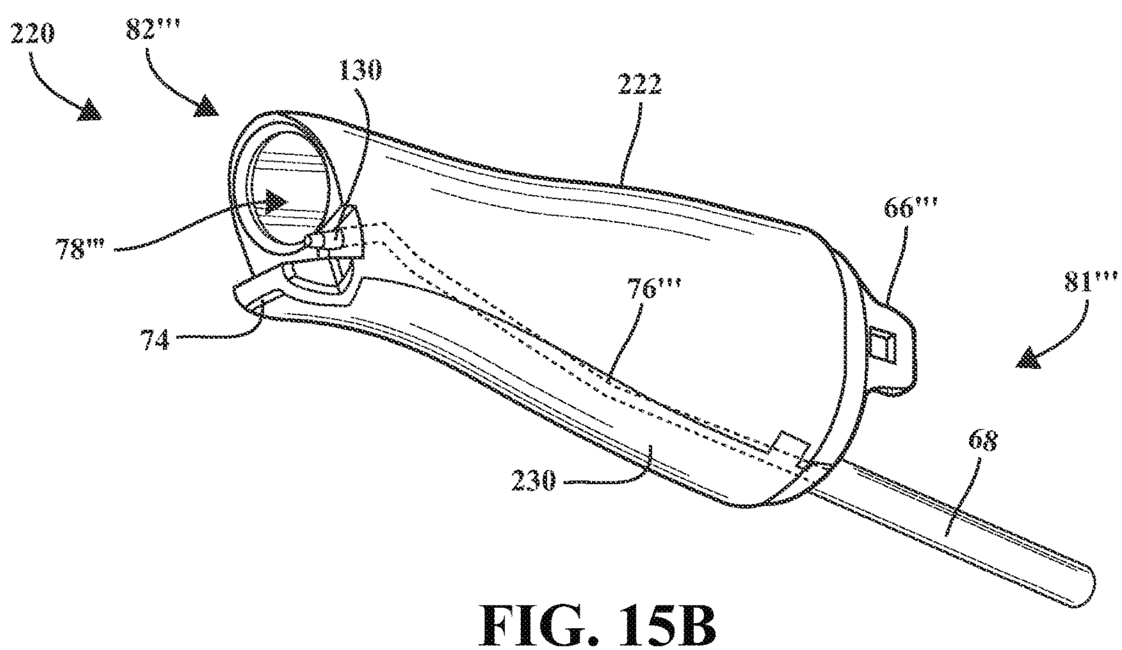

FIGS. 15A and 15B illustrate an alternative carrier 220 that may be incorporated into the distal handpiece assembly 28 and likewise carries many of the above advantages. The carrier 220 may include a carrier base 222, which may be a defined as a single, monolithic component that fully defines at least lumen 78'" of the carrier 220 for receiving a vibratory component of the ultrasonic surgical instrument 10 as described above. The carrier base 222 may be made via injection molding. It is also contemplated that the carrier base 222 could be made using additive manufacturing (e.g., 3D printing) techniques or machining techniques. In some implementations, similar to the single piece carrier 64, the carrier base 222 may be formed around the conduit 50. Alternatively, the carrier base 222 may be produced with an empty lumen 224, such as using a removeable pin, and a portion of the conduit 50 may thereafter be inserted through the lumen 224. The carrier base 222 may further be formed at its proximal region 81'" with proximally extending tabs 66'" for engaging corresponding features of the proximal handpiece assembly 26 as described herein.

The carrier base 222 may include an outer surface 226 defining a trench 228 for receiving the flexible conductor 70. The lumen 224 may be in communication with the trench 228 such that, following or during production of the carrier 220, the conduit 50 may run through at least a portion of the length of the trench 228 from the proximal region 81'" of the carrier base 222 and through the lumen 224 as shown in the illustrated example.

The carrier 220 may further include a conductor housing component 230 for holding and coupling the flexible conductor 70 to the carrier base 222. The conductor housing component 230 may be couplable to the outer surface 226 of the carrier base 222, or more particularly the trench 228 of the carrier base 222, and shaped so as to run the length of the of the carrier base 222. As previously mentioned, the carrier base 222 may fully define lumen 78", thus increasing the integrity of the carrier 220 relative to using multiple components to form the lumen 78'''.

The conductor housing component 230 may similarly define a trench 232 for receiving the flexible conductor 70. The conductor housing component 230 may be configured to be received in the trench 228 of the carrier base 222 to form a retaining fit therewith, and correspondingly hold the flexible conductor 70 between the carrier base 222 and the conductor housing component 230. To this end, the conductor housing component 230 may include tabs 234 configured to engage corresponding recesses 235 formed adjacent the trench 228 of the carrier base 222, such as via a friction fit, and a distally extending wedge-shaped feature 236 located at a distal region of the trench 232 of the conductor housing component 230. The wedge-shaped feature 236 may be configured to engage a complementary oblique portion 238 of the trench 228 of the carrier base 222, such as via a friction fit. The wedge-shaped feature 236 and complementary oblique portion 238 may each be shaped to correspond to that of the transceiver 74 of the flexible conductor 70, so as to hold the transceiver 74 therebetween as illustrated in FIG. 15B. It is also contemplated that the conductor housing component 230 may be coupled to the carrier base 222 via a weld, adhesive, or similar bonding process.

In some implementations, the conductor housing component 230 may also include a trench 240 for receiving the length of the conduit 50 running through the trench 228 of the carrier base 222 when the conductor housing component 230 is received within the trench 228. Hence, when the conductor housing component 230 is received within the trench 228, the lumen 224 of the carrier base 222 and the trench 228 may thus form a lumen 76''' of the carrier 220 through which the irrigation conduit 50 runs. Once assembled, the carrier 220 may be over molded as described above.

Figure 17:
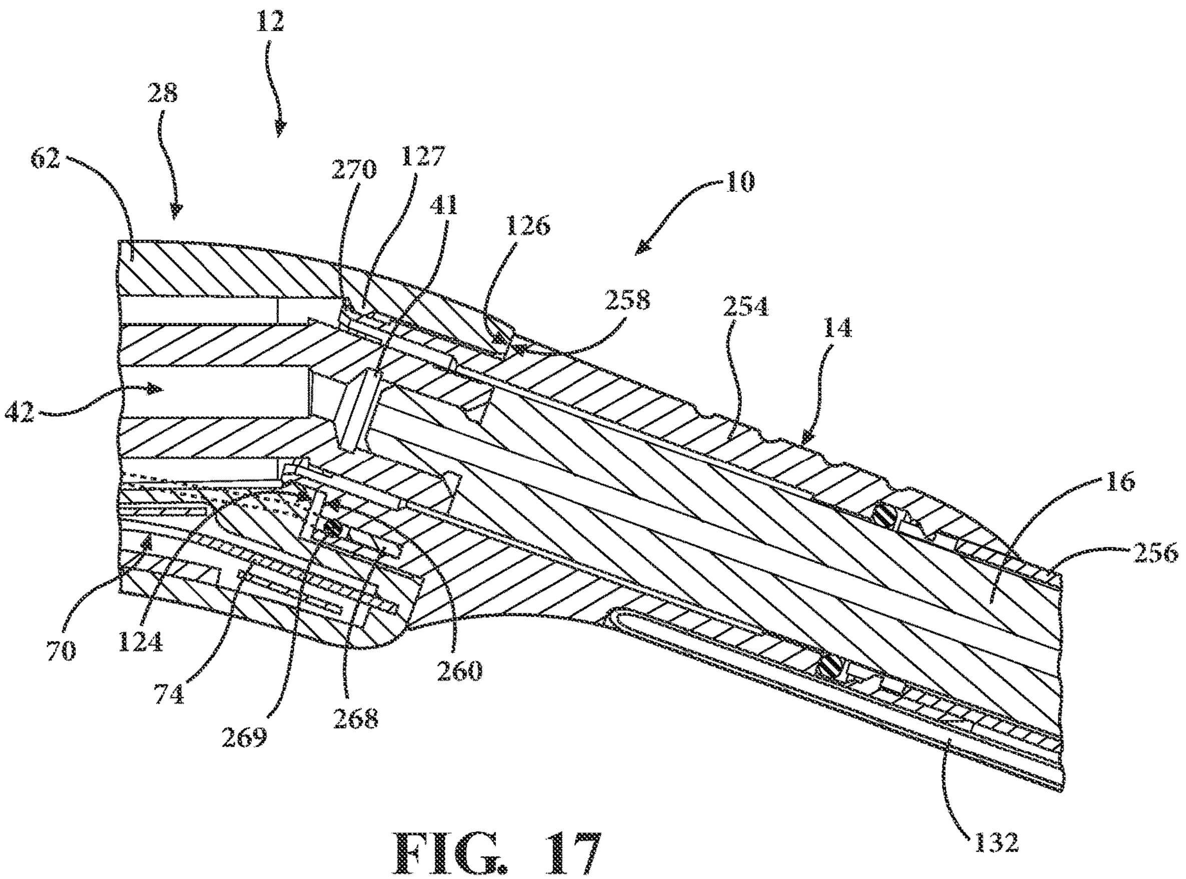
FIG. 17 illustrates a cross section taken along a longitudinal length of the distal handpiece assembly and tip sleeve when coupled to one another.

Referring to FIGS. 16 and 17, an exemplary configuration of the interface between the distal handpiece assembly 28 and the sleeve 14 and/or ultrasonic tip 16 is illustrated. FIG. 16 illustrates the distal region of the distal handpiece assembly 28, which may also be referred to herein as the distal region of the ultrasonic handpiece 12. As described above, the distal region of the ultrasonic handpiece 12 may comprise an attachment region 120, such as formed in the overmold assembly 62, configured to serve as the interface between the ultrasonic handpiece 12 and the sleeve 14 and/or the ultrasonic tip 16. The attachment region 120 may comprise a recess 122 defined by a distally-directed face 124 and a distal surface 126 of the overmold assembly 62 that are connected by a plurality of walls 128 extending perpendicular to the distally-directed face 124 and the distal surface 126. The distally-directed face 124 may comprise a coupling feature 127, which may comprise a tab, lip, or similar snap fit coupling mechanism.

The distal end of the horn 40 may be configured to partially extend through an aperture 252 defined in the distally-directed face 124, such that at least a portion of the horn 40 and the threaded coupler 41 are disposed within the recess 122 at the distal end of the ultrasonic handpiece 12. The lumen 42 that extends through the horn 40 may similarly open to the recess 122.

Extending into the recess 122 from the distally-directed face 124 may be a coupler 130 positioned at the distal end of the conduit 50 defining the lumen 52 through the ultrasonic handpiece 12. The coupler 130 may comprise a fitting, hose barb, or similar coupling member for coupling the distal end of the conduit 50 to a corresponding conduit 132 of the sleeve 14. The coupler 130 may serve as an inlet or an outlet to transport material and/or fluid between the ultrasonic handpiece 12 and sleeve 14. For instance, the coupler 130 may be configured to be in fluid communication with the lumen 52 disposed within the ultrasonic handpiece 12 to provide irrigation fluid to the sleeve 14.

As shown in the illustrated example, the sleeve 14 may comprise a hub 254 positioned at a proximal end of the sleeve 14 and a sleeve body 256 that extends distally from the hub 254. The sleeve 14 may comprise a lumen 54 defined by the hub 254 and sleeve body 256 that extends the length of sleeve 14 and is configured to surround at least a portion of the ultrasonic tip 16 when coupled to the ultrasonic handpiece 12. The hub 254 may comprise a protrusion 257 that extends proximally from a distal surface 258 of the hub 254 and terminates at a proximal surface 260. The proximal surface 260 of the protrusion 257 may be oriented to be generally parallel to the distal surface 258. The shape of the protrusion 257 may be defined by a plurality of external circumferential surfaces 262 or wall members that extend between the distal surface 258 and the proximal surface 260 and are configured to define the outer perimeter of the protrusion 257. The external circumferential surfaces 262 may be oriented to be generally perpendicular to the proximal surface 260 and/or the distal surface 258. It should be appreciated the shape of the protrusion 257 is positioned to fit closely within the recess 122, such that the external circumferential surfaces 262 of the protrusion 257 engage the walls 128 of the recess 122.

While not illustrated in the figures, it is further contemplated that the external circumferential surfaces 262 of the protrusion 257 may be oriented at an angle other than 90 degrees relative to the proximal surface 260 and/or the distal surface 258 in order to create a tapered protrusion 257. For example, the area defined by the external circumferential surfaces 262 of the protrusion 257 proximate the distal surface 258 may be greater than the area of the proximal surface 260.

The hub 254 may further comprise a fitting 264 extending from the proximal surface 260 of the protrusion 257. The fitting 264 may be configured to couple to the corresponding coupler 130 of the ultrasonic handpiece 12. The fitting 264 of the sleeve 14 and corresponding coupler 130 of the ultrasonic handpiece 12 may be configured to facilitate the exchange of fluid between the sleeve 14 and the ultrasonic handpiece 12. In particular, the coupler 130 may be sized to fit within the fitting 264 when the sleeve 14 is coupled to the ultrasonic handpiece 12. For example, irrigation fluid from the ultrasonic handpiece 12 may be dispersed to the sleeve 14 through the connection of the fitting 264 to the coupler 130. This eliminates the need to connect the sleeve to an irrigation line that is separate from the ultrasonic handpiece 12, e.g., such as an irrigation line that connects to a side of the sleeve 14. Alternatively, a vacuum may be applied to the ultrasonic handpiece 12 configured to aspirate material from the sleeve 14 through the fitting 264 and coupler 130 when coupled in an alternative configuration.

The sleeve 14 may further comprise a conduit 132 formed in the sleeve body 256 that runs adjacent to the lumen 54 of the sleeve 14. The fitting 264 may be coupled to the proximal end of the conduit 132. The conduit 132 may be configured to channel irrigation fluid through the sleeve 14 separate from the lumen 54 of the sleeve 14. The conduit 132 may be routed in various ways through the sleeve 14.

The hub 254 may further comprise a cavity 266 in the protrusion 257 that that includes an opening in the proximal surface 260 of the protrusion 257. The cavity 266 may be configured to at least partially enclose a tag 268, antenna, transceiver, or similar wireless communication device that is configured to communicate with the transceiver 74 disposed in the distal handpiece assembly 28 of the ultrasonic handpiece 12. For example, the tag 268 may comprise an RFID tag 268 that may be inserted and/or disposed within the cavity 266. While the figures illustrate the cavity 266 and RFID tag 268 as being positioned generally near the proximate end of the sleeve 14, it should be understood that the cavity 266 and RFID tag 268 may be positioned at other locations on or within the sleeve 14. For example, the RFID tag 268 may be positioned within one of the other external circumferential surfaces 262A, 262B, or 262D of the protrusion 257. Alternatively, the cavity 266 and RFID tag 268 may be positioned within the distal surface 258 of the hub 254.

The RFID tag 268 may include a memory unit that stores data and/or information related to one or more properties or characteristics related to the sleeve 14 and ultrasonic tip 16. For example, the RFID tag 268 may comprise information identifying the type of cutting feature 18 disposed on the distal end of the ultrasonic tip 16. The RFID tag 268 may also comprise information identifying the type of sleeve 14. The stored data and/or information may also include ultrasonic handpiece 12 compatibility settings. This information may be communicated to the ultrasonic handpiece 12 and subsequently the control console 24 so that the control console 24 may modify power settings, irrigation settings, aspiration settings, and/or other settings intended to optimize the efficiency of the cutting feature 18 of the ultrasonic tip 16.

The RFID tag 268 may also be used to prevent customers from reusing an ultrasonic tip 16 and/or sleeve 14 as part of a sterilization standard or procedure. For example, the ultrasonic tip 16 and sleeve 14 may be configured as a single use component that is not intended to be sterilized and reused. The RFID tag 268 may also include a coil 269. The shape of the protrusion 257 and the recess 122 may be arranged such that the plane defined by the coil 269 of the RFID tag 268 is generally parallel to the plane defined by the transceiver 74.

The RFID tag 268 in the sleeve 14 may be understood as a tip memory. The ultrasonic tip 16 and the sleeve 14 are typically packaged together in a kit. The data contained in the RFID tag 268 may be used control actuation of the ultrasonic tip 16. The coil 269 embedded in the sleeve 14 may be coupled to memory unit of the RFID tag 268. As described above, the RFID tag 268 may be used to prevent customers from reusing ultrasonic tip 16 and/or sleeve 14. In combination with the memory unit, the RFID tag 268 may be further configured to track and/or count the number of uses and limit the number of times a tip 16 is used. For example, the RFID tag 268 may be configured to store on the memory unit the number and/or amount of time the ultrasonic tip 16 and sleeve 14 are operated. The RFID tag 268 and memory unit may be configured to prevent actuation of the tip after a defined number of uses. The defined number of uses may be based on wear and effectiveness of the ultrasonic tip 16 and/or sleeve 14, in order to prevent reduced efficiency or failure during an operation.

While not illustrated, the ultrasonic handpiece 12 may also include a memory. The memory may contain data describing the characteristics of the ultrasonic handpiece 12. Memory may take the form of an EPROM, an EEPROM or be included within an RFID tag as described above. The memory, in addition to containing data capable of being read, may be able to store data written to the memory after manufacture of the ultrasonic handpiece 12. Ancillary components not illustrated may be mounted to the ultrasonic handpiece 12 to facilitate the reading of data from and the writing of data to the memory. These components may include or consist of one or more of the following: conductors; exposed contacts/contact pins; a coil/antenna; or an isolation circuit.

The tag 268 may be secured in the cavity 266 by a pin. The pin may comprise a plastic or alloy material and be configured to create a friction fit within the opening of the cavity 266 to secure the RFID tag 268 within the cavity 266 and protect it from being damaged. Alternatively, the pin may comprise a seal such as an elastomeric O-ring. In yet another configuration, the pin may comprise an epoxy, glue, sealant, or similar compound configured to secure the tag 268 within the cavity 266 and protect the tag from damage. It is further contemplated that the RFID tag 268 may be injection molded or heat staked into the sleeve 14. The RFID may also take other forms of tags.

The protrusion 257 may be configured in a complementary shape to the one defined by the recess 122 at the distal end of the ultrasonic handpiece 12, wherein the protrusion 257 is configured to be disposed within the recess 122 when the sleeve 14 is coupled to the ultrasonic handpiece 12. Furthermore, the shape of the recess 122 and the protrusion 257 may be configured to align the sleeve 14 relative to the ultrasonic handpiece 12, as well as prevent rotational movement of the sleeve 14 relative to the ultrasonic handpiece 12. For example, as illustrated in FIG. 16, the recess 122 of the ultrasonic handpiece 12 comprises a plurality of walls 128 that define the perimeter of the recess 122. In the example configuration of the recess 122 illustrated in FIG. 16, the walls 128A, 128B, 128C, and 128D define a doghouse-like shape, wherein you have two opposing walls 128A, 128B, that are generally parallel to one another. The two opposing walls 128A, 128B are connected by a third wall 128C that is generally perpendicular to the two opposing walls 128A, 128B. A fourth wall 128D, that connects the two opposing walls 128A, 128B opposite the third wall 128C, may comprise a generally arch-like shape. The plurality of external circumferential surfaces 262A, 262B, 262C, and 262D that define the outer perimeter of the protrusion 257 may then be configured to define a doghouse-like shape that corresponds to the shape of the recess 122.

While not illustrated in the figures, it is contemplated that the walls 128A, 128B, 128C, and 128D of the recess 122 and the corresponding external circumferential surfaces 262A, 262B, 262C, and 262D of the protrusion 257 may be configured to define alternative shapes. For example, the walls 128 and external circumferential surfaces 262 may define a rectangular shape, a star shape, an oval shape, a triangular shape or other similar shape. While the protrusion 257 and the recess 122 illustrated in the figures include complementary shapes, it is further also contemplated that the protrusion 257 and the recess 122 may have slightly different shapes, so long as the protrusion 257 may be disposed within the recess 122. For example, the protrusion 257 on the sleeve 14 may be configured to comprise several more external circumferential surfaces 262 to the protrusion by creating a chamfer between the surfaces 262C and 262A and/or 262B and it would still insert and function in the ultrasonic handpiece 12.

The shape of the protrusion 257 and the recess 122 may further be configured to orient the tag 268 that is disposed in the cavity 266 of the hub 254 relative to the transceiver 74 disposed in the distal handpiece assembly 28 of the ultrasonic handpiece 12. Utilizing the shape of the protrusion 257 and the recess 122 to orient the tag 268 relative to the transceiver 74 can improve the reliable establishment of communication between the tag 268 relative and the transceiver 74. For example, as illustrated in FIG. 16, the tag 268 and the transceiver 74 are positioned such that the tag 268 and the RFID tag 268 at least partially overlap in an axial sense when the sleeve 14 is coupled to the ultrasonic handpiece 12. Furthermore, the cavity 266 in the hub 254 and the portion of the distal handpiece assembly 28 receiving the transceiver 74 may be oriented such that a first longitudinal axis of the tag 268 and a second longitudinal axis of transceiver 74 are generally parallel to one another. The protrusion 257 and the distal handpiece assembly 28 may further be configured to reduce the distance between the cavity 266 in the hub 254 and the portion of the distal handpiece assembly 28 holding the transceiver 74 to further improve communication between the tag 268 and the transceiver 74.

The hub 254 may further comprise a plurality of retention fingers 270 that extend distally from the proximal surface 260 of the protrusion 257. The plurality of retention fingers 270 may be spaced about the perimeter of the lumen 54 defined in the proximal surface 260. The plurality of retention fingers 270 may further comprise a tab 272, bump, or protrusion configured to engage the coupling feature 127 at the perimeter of the aperture 252 in the distally-directed face 124 of the recess 122 in the ultrasonic handpiece 12. The tab 272 of each of the plurality of retention fingers 270 may engage the coupling feature 127 of the recess 122 to create a snap-fit and/or friction fit to removably couple the sleeve 14 to the ultrasonic handpiece 12. The plurality of retention fingers 270 may comprise a very compliant material like a silicone rubber, or a metal material such as a leaf spring. While not illustrated in the figures, it is contemplated that the sleeve 14 may be coupled to the ultrasonic handpiece 12 in a number of other ways. For example, the hub 254 hub may be configured without and retention fingers 270, and the coupler 130 of the ultrasonic handpiece 12 may be mated with the fitting 264 of the sleeve 14 to form the primary retention mechanism. In yet another configuration, the protrusion 257 may comprise a compliant material, which contains the RFID tag 268 despised within a slit in the material, and the protrusion 257 may create an interference fit with the recess 122.

Referring to FIG. 17, a sectional view of an example configuration of the interface between the distal handpiece assembly 28 of the ultrasonic handpiece 12 and the sleeve 14 and ultrasonic tip 16 is illustrated. As illustrated in FIG. 17, the distal surface 126 of the distal handpiece assembly 28 may abut the distal surface 258 of the protrusion 257 when the sleeve 14 is coupled to the ultrasonic handpiece 12. This may assist in forming a stable connection between the sleeve 14 to the ultrasonic handpiece 12. Similarly, the distally-directed face 124 of the distal handpiece assembly 28 may abut the proximal surface 260 of the protrusion 257 when the protrusion 257 is disposed within the recess 122 to couple the sleeve 14 to the ultrasonic handpiece 12. However, it is also possible that there may be a gap between the distally-directed face 124 of the distal handpiece assembly 28 and the proximal surface 260 of the protrusion 257 when the distal surface 126 of the distal handpiece assembly 28 abuts the distal surface 258 of the protrusion 257.

The above disclosure provides examples of providing a distal handpiece assembly for an ultrasonic surgical instrument. It is also contemplated that the above examples can be applied to other types of surgical instruments, such as a motorized driver, drill, saw, or shaver. For instance, the above examples may be applied to a handpiece assembly for such other types of surgical instruments so as to provide a handpiece assembly including an overmold assembly and a carrier as described above. The carrier may be a single piece carrier and define a lumen for receiving a power generating component (e.g., motor) and/or power transfer component (e.g., driving shaft, end effector shaft) of the surgical instrument, and may define a trench for receiving a flexible conductor, which may include an antenna for communicating with another component of the surgical instrument. The overmold assembly may include a coupling feature for coupling the handpiece assembly to one or more other components of the surgical instrument.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the present invention may be practiced otherwise than as specifically described.

Some examples are described with reference to the following clauses:

Clause 1. A method of making a surgical tool assembly comprising: providing a single piece carrier defining a lumen extending between proximal and distal regions of the single piece carrier, the lumen sized to receive a power generating and/or transfer component of the surgical tool, wherein an outer surface of the single piece carrier defines a trench extending between the proximal and distal regions of the single piece carrier and defines at least one retention member adjacent to the trench; positioning a flexible conductor including an antenna disposed in a distal region of the flexible conductor in the trench and adjacent the at least one retention member such that the retention member retains the flexible conductor within the trench and the antenna is disposed adjacent the distal region of the single piece carrier; and after positioning the flexible conductor, overmolding the single piecer carrier to form an overmold assembly over the single piece carrier that comprises a coupling feature for coupling the overmold assembly to one or more other components of the surgical tool.

Clause 2. The method of clause 1, wherein the at least one retention member is defined as at least one post or at least one tab extending transversely over the trench.

Clause 3. The method of clause 1 or clause 2, wherein the single piece carrier defines a slot in at least one of an outer distally directed face and an outer proximally directed face of the single piece carrier, the slot being in communication with the trench and configured to receive a portion of the flexible conductor.

What is claimed is:

1. A method of making an ultrasonic surgical instrument assembly, the method comprising:

providing a single piece carrier defining a lumen extending between proximal and distal regions of the single piece carrier and sized to receive a vibratory component of the ultrasonic surgical instrument, wherein an irrigation conduit separated from the lumen extends through the single piece carrier between the proximal and distal regions of the single piece carrier, and an outer surface of the single piece carrier defines a trench extending between the proximal and distal regions of the single piece carrier and defines at least one tab extending transversely over the trench;

positioning a flexible conductor within the trench of the single piece carrier such that the flexible conductor runs under the at least one tab; and after positioning the flexible conductor, overmolding the single piece carrier to form an overmold assembly comprising a distal coupling feature for coupling the overmold assembly to a tip sleeve of the ultrasonic surgical instrument.

2. The method of claim 1, comprising injection molding the single piece carrier defining the lumen, the trench, and the at least one tab.

3. The method of claim 2, comprising injection molding the single piece carrier around the irrigation conduit.

4. The method of claim 2, comprising:

horizontally suspending the irrigation conduit within a carrier injection mold tool using at least one support disposed at an intermediate portion of the irrigation conduit; and injection molding the single piece carrier around the irrigation conduit to form a second lumen around the irrigation conduit and extending between the proximal and distal regions.

5. The method of claim 4, comprising injection molding the single piece carrier around the irrigation conduit and the at least one support to form the second lumen around the irrigation conduit and at least one through passage extending between the second lumen and the outer surface of the single piece carrier.

6. The method of claim 3, wherein the single piece carrier comprises an inner surface defining the lumen, and comprising forming with a pin of a carrier injection mold tool a trench in the inner surface and adjacent the irrigation conduit during the injection molding of the single piece carrier for limiting movement of the irrigation conduit relative to the single piece carrier.

7. The method of claim 1, wherein the flexible conductor comprises an antenna disposed at a distal region of the flexible conductor, and comprising inserting the flexible conductor into the trench by sliding a proximal end of the flexible conductor into the trench from the distal region to the proximal region of the single piece carrier such that the antenna is disposed adjacent the distal region of the single piece carrier.

8. The method of claim 1, wherein an antenna is disposed at a distal region of the flexible conductor, and a distal region of the trench comprises an enlarged section for receiving the antenna when the flexible conductor is inserted into the trench.

9. The method of claim 1, wherein the overmold assembly includes a proximal coupling feature for coupling the single piece carrier to a proximal housing assembly of the ultrasonic surgical instrument.

10. The method of claim 9, wherein the proximal region of the single piece carrier comprises proximally facing protrusions for aligning a transducer disposed in the proximal housing assembly when coupling the proximal housing assembly to the single piece carrier.

11. The method of claim 1, comprising injection molding the overmold assembly around the single piece carrier with the irrigation conduit and flexible conductor.

12. The method of claim 11, wherein the distal region of the single piece carrier includes a first touch off feature facing a longitudinal axis of the lumen and a second touch off feature facing a distal end of the single piece carrier, each of the first touch off feature and the second touch off feature configured to contact a portion of an overmold injection mold tool to limit movement of the distal region of the single piece carrier during the injection molding of the overmold assembly around the single piece carrier.

* * * * *